United States Patent
Saito

(10) Patent No.: US 12,247,972 B2
(45) Date of Patent: Mar. 11, 2025

(54) METHOD FOR MEASURING INTRACELLULAR POTENTIAL WITH A CAPACITANCE TYPE POTENTIAL MEASUREMENT DEVICE

(71) Applicant: ION CHAT RESEARCH CORPORATE, Saitama (JP)

(72) Inventor: Mitsuyoshi Saito, Tokyo (JP)

(73) Assignee: ION CHAT RESEARCH CORPORATE, Saitama (JP)

(*) Notice: Subject to any disclaimer, the term of this patent is extended or adjusted under 35 U.S.C. 154(b) by 1125 days.

(21) Appl. No.: 17/050,759

(22) PCT Filed: Apr. 26, 2019

(86) PCT No.: PCT/JP2019/018158
§ 371 (c)(1),
(2) Date: Oct. 26, 2020

(87) PCT Pub. No.: WO2019/208828
PCT Pub. Date: Oct. 31, 2019

(65) Prior Publication Data
US 2021/0231637 A1    Jul. 29, 2021

(30) Foreign Application Priority Data

Apr. 27, 2018    (JP) .................................. 2018-087689

(51) Int. Cl.
*G01N 33/483* (2006.01)
*G01N 27/22* (2006.01)
(Continued)

(52) U.S. Cl.
CPC ......... *G01N 33/483* (2013.01); *G01N 27/226* (2013.01); *G01N 33/15* (2013.01);
(Continued)

(58) Field of Classification Search
None
See application file for complete search history.

(56) References Cited

U.S. PATENT DOCUMENTS 5,622,868 A * 4/1997 Clarke ................. G01N 21/171
436/151
5,981,268 A   11/1999 Kovacs et al.
(Continued)

FOREIGN PATENT DOCUMENTS

CN    1154475 A    7/1997
CN    1643132 A    7/2005
(Continued)

OTHER PUBLICATIONS

Wang et al., Magnetic Measurement and Stimulation of Cellular and Intracellular Structures, 2020, ACS Nano, vol. 14, Issue 1 (Year: 2020).*

(Continued)

*Primary Examiner* — Maris R Kessel
*Assistant Examiner* — Mickey Huang
(74) *Attorney, Agent, or Firm* — ArentFox Schiff LLP; Daniel W. Clarke

(57) ABSTRACT

The purpose of the present invention is to provide a method for accurately measuring and controlling intracellular potential by a simple method that is less invasive to the cell and does not require a skilled technique. The method according to the present invention comprises: by using magnetic force from a magnetic electrode adhered to the surface of a target cell, into which conductive nanoparticles have been preliminarily introduced, or a magnet being in contact with a conductive plate electrode, attracting the conductive nanoparticles inside the cell to the side of the cell surface adhering to the electrode, and then allowing the conductive nanoparticles to pass through the cell membrane to thereby (Continued)

bring the end outside the cell into contact with the magnetic electrode or the conductive plate electrode; or alternatively, adhering the conductive nanoparticles adsorbed on the magnetic electrode surface to the upper side of the target cell, and allowing the conductive nanoparticles to pass through the cell membrane by attracting the conductive nanoparticles to an iron plate disposed on the lower side of the cell to thereby leave the end outside the cell being in contact with the magnetic electrode. A capacitor is fabricated by using the conductive plate in contact with the conductive nanoparticles together with a conductive plate (an aluminum foil). Alternatively, a capacitor is fabricated by disposing a magnetic body via an insulating body on the upper side of the magnetic electrode. This capacitor detects, as a sensor, a change in charge inside the target cell and converts the same into a voltage change to thereby enable the measurement of the intracellular potential. The present invention also makes it possible to monitor the effect of a test reagent, said test reagent being administered to an extracellular solution, on a cell.

5 Claims, 13 Drawing Sheets

Specification includes a Sequence Listing.

(51) Int. Cl.
G01N 27/30 (2006.01)
G01N 33/15 (2006.01)
G01N 33/50 (2006.01)
G01N 33/543 (2006.01)

(52) U.S. Cl.
CPC ..... *G01N 33/5058* (2013.01); *G01N 33/5061* (2013.01); *G01N 27/30* (2013.01); *G01N 33/54346* (2013.01)

(56) References Cited

U.S. PATENT DOCUMENTS

| 2003/0091980 A1 | 5/2003 | Lynch et al. |
| 2004/0146849 A1* | 7/2004 | Huang ............ G01N 33/48728 435/287.1 |
| 2005/0064578 A1 | 3/2005 | Muller-Hartmann et al. |
| 2010/0330612 A1 | 12/2010 | Sorensen |
| 2012/0034622 A1 | 2/2012 | Ignatius et al. |
| 2013/0230881 A1 | 9/2013 | Yasuda et al. |
| 2014/0349332 A1 | 11/2014 | Yasuda et al. |
| 2016/0011176 A1 | 1/2016 | Yasuda et al. |

FOREIGN PATENT DOCUMENTS

| CN | 101859908 A | | 10/2010 |
| CN | 105424771 A | * | 3/2016 |
| EP | 3628744 A1 | | 4/2020 |
| JP | 2005505761 A | | 2/2005 |
| WO | 2012/043820 A1 | | 4/2012 |
| WO | 2013/061849 A1 | | 5/2013 |
| WO | 2014/098182 A1 | | 6/2014 |
| WO | 2018/199334 A1 | | 11/2018 |

OTHER PUBLICATIONS

Mitsuyoshi L. Saito, NanoTouch: intracellular recording using transmembrane conductive nanoparticles, J Neurophysiol. Nov. 1, 2019; 122(5): 2016-2026. (Year: 2019).*

Daisuke Kami, et al., "Application of Magnetic Nanoparticles to Gene Delivery," International Journal of Molecular Sciences, vol. 12, No. 6, Jun. 2011, pp. 3705-3722.

Extended European Search Report of European Patent Application No. 19793819.4 mailed on Dec. 22, 2021.

Fendyur, A., et al., "Toward on-chip, in-cell recordings from cultured cardiomyocytes by arrays of gold mushroom-shaped microelectrodes," Frontiers in Neuroengineering, 2012, 5:21.

Khudhair, D., et al.,(2017) Microelectrode Arrays: Architecture, Challenges and Engineering Solutions. In: Bhatti A., Lee K., Garmestani H., Lim C. (eds) Emerging Trends in Neuro Engineering and Neural Computation. Series in BioEngineering. Springer, Singapore, pp. 41-59.

Levy, R., et al., "Gold nanoparticles delivery in mammalian live cells: a critical review", 2010, Nano Reviews, 1: 4889—DOI: 10.3402/nano.v1i0.4889.

Spira, M., et al., "Multi-electrode array technologies for neuroscience and cardiology", Nature Nanotechnology, 2013, 8:83-94.

First Office Action of Chinese Application No. 201980028400.4 mailed Feb. 12, 2023, along with English language translation thereof.

Second Office Action in Chinese Application No. 201980028400.4 dated Sep. 3, 2023 (with English translation), 20 pages.

* cited by examiner

Gold coated magnetic particles, which are introduced in the cells, are drawn by the magnet, penetrate the cell membrane, and act as electrodes that connect the inside and outside of the cell FIG. 16A
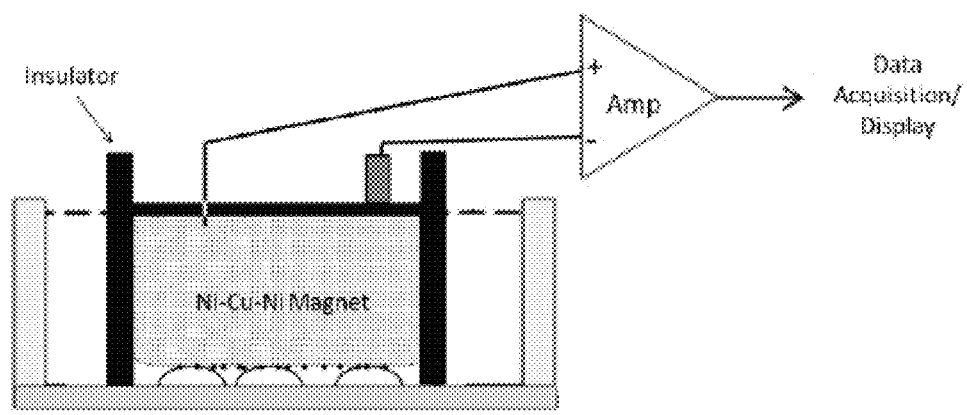
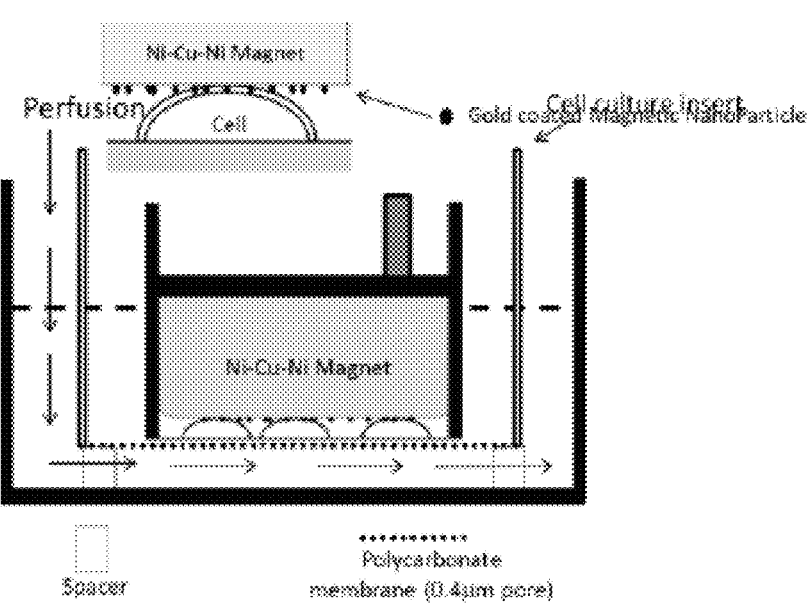
FIG. 16B

```
                           SEQUENCE LISTING

<160> NUMBER OF SEQ ID NOS: 6

<210> SEQ ID NO 1
<211> LENGTH: 38
<212> TYPE: DNA
<213> ORGANISM: Artificial Sequence
<220> FEATURE:
<223> OTHER INFORMATION: ChRWR sense primer

<400> SEQUENCE: 1
cactataggg aagctaccat ggctcggaga ccctggct                          38

<210> SEQ ID NO 2
<211> LENGTH: 38
<212> TYPE: DNA
<213> ORGANISM: Artificial Sequence
<220> FEATURE:
<223> OTHER INFORMATION: ChRWR antisense primer

<400> SEQUENCE: 2
atagaatagg aagctctact tgcctgtccc tttgttga                          38

<210> SEQ ID NO 3
<211> LENGTH: 20
<212> TYPE: DNA
<213> ORGANISM: Artificial Sequence
<220> FEATURE:
<223> OTHER INFORMATION: KIR2.1 1st sense primer

<400> SEQUENCE: 3
ccaaagcaga agcactggag                                              20

<210> SEQ ID NO 4
<211> LENGTH: 22
<212> TYPE: DNA
<213> ORGANISM: Artificial Sequence
<220> FEATURE:
<223> OTHER INFORMATION: KIR2.1 1st A/S

<400> SEQUENCE: 4
ctttgaaacc attgtgcttg cc                                           22

<210> SEQ ID NO 5
<211> LENGTH: 39
<212> TYPE: DNA
<213> ORGANISM: Artificial Sequence
<220> FEATURE:
<223> OTHER INFORMATION: KIR2.1 ICR HindIII sense

<400> SEQUENCE: 5
cactataggg aagctaccat gggcagtgtg cgaaccaac                         39

<210> SEQ ID NO 6
<211> LENGTH: 36
<212> TYPE: DNA
<213> ORGANISM: Artificial Sequence
<220> FEATURE:
<223> OTHER INFORMATION: KIR2.1 ICR HindIII A/S

<400> SEQUENCE: 6
atagaatagg aagcttcata tctccgactc tcgccg                            36
```

METHOD FOR MEASURING INTRACELLULAR POTENTIAL WITH A CAPACITANCE TYPE POTENTIAL MEASUREMENT DEVICE

RELATED APPLICATIONS

This application is a national stage application, filed under 35 U.S.C. § 371, of International Application No. PCT/JP2019/018158, filed on Apr. 26, 2019, which claims the benefit of priority under 35 U.S.C. § 119 (e) to Japanese Application No. 2018-087689, filed on Apr. 27, 2018, each of which is incorporated herein by reference in its entirety.

INCORPORATION BY REFERENCE OF SEQUENCE LISTING

Sequence Listing

The contents of the text file named "55708_901N01US_Sequence_Listing.txt," which was created on Oct. 21, 2019 and is 1.39 KB in size, are hereby incorporated by reference in their entirety.

TECHNICAL FIELD

The present invention relates to a method for measuring the intracellular membrane potential (intracellular potential) by combining the principle of a charge amplifier with a capacitance-type potential measurement device (Capacitive potential detection device).

BACKGROUND ART

All cells have different ionic compositions inside and outside the cell, and the intracellular potential (membrane potential) is maintained by a transporter (e.g. sodium pump) that keeps the difference in ion distribution and the difference in ionic composition. In the resting state, the membrane potential is stable (resting membrane potential). However, when the ion channels on the cell membrane surface are activated and the ion channels are opened, ions are released or flow in at once through the ion channels due to the difference in ion concentration inside and outside the cell membrane. As a result, the electric potential of the entire cell to change (depolarization or hyperpolarization occurs), and consequently, the intracellular membrane potential changes. As a result, the generation/transmission of action potentials occurs in the myocardium and nerves in which then, an information transmission occurs, such as the release of hormones and neurotransmitters and the contraction of myocardial and skeletal muscle cells.

Conventionally, changes in cell membrane potential and accompanying measurement of membranes current through ion channels have been used to observe changes in the cell state and the cell response to drugs. In drug discovery screening, in particular, drug candidates are exposed to cultured cardiomyocytes and nerve cells and other cells, and changes in membrane potential are measured to assess cardiotoxicity and neurotoxicity.

In order to measure the intracellular potential, conventionally, a metal electrode or a micro glass electrode is filled with an electrolytic solution, inserted into the cell, and then the current or voltage is measured from the potential difference with the extracellular electrode. Measurement method called the patch clamp has become the industry standard method. The patch clamp method precisely measures and controls intracellular potential changes by bringing a glass pipette filled with intracellular electrolyte into close contact with the cell membrane and electrically integrates the glass pipette and cells.

The patch clamp method is subdivided into two different recording modes. A whole cell mode for measuring the dynamics of ion channels expressed in the whole cell, and a method for measuring the dynamics of a single channel (single channel activity) that is contained in only the cell membrane within the inner diameter of the patch pipette (cell mode). Then, there is a method (inside patch, outside patch mode) in which the microcell membrane is separated from the cells and measured.

In the whole cell mode, changes in intracellular potential and dynamics of current (ion channel activity) passing through ion channels throughout the cell are measured by breaking through the cell membrane inside the electrode bonded to the glass pipette. The above procedure requires a highly skilled technique and a high degree of expertise because it is a recording method performed by using electrodes directly on individual cells under a microscope.

These intracellular recording methods (voltage-clamp, current-clamp) can observe the dynamics of how ions pass through ion channels in the cell membrane, as represented by the patch-clamp method (whole-cell patch-clamp). In the voltage-clamp mode, the feedback function included in the patch-clamp amplifier efficiently controls the intracellular potential, and the fast (in milliseconds) phenomenon that occurs due to the opening and closing of the ion channel can be recorded as an electric current change. In the current-clamp mode, the action on the cell due to the activity of the ion channel can be recorded as a (membrane) potential change.

There are manual patch-clamp method and auto patch method in the patch-clamp method. Among those, the manual patch-clamp method has high reliability of data in electrophysiological measurement.

However, the manual patch-clamp method is very inefficient because an operator uses a microscope to operate a manipulator to perform an experiment and requires a large amount of specialized knowledge. This has become a major hurdle in medical biology research, especially in the field of drug discovery.

On the other hand, the auto patch-clamp method uses an automated electrophysiological measuring instrument, and although its performance has improved remarkably in recent years, the reliability of data is not as reliable as replacing the manual patch-clamp method. Furthermore, the auto patch-clamp test equipment is so expensive that its use is limited to large pharmaceutical companies.

In recent years, a method similar to the patch clamp method was developed but high voltage is applied when penetrating an electrode into a cell membrane in order to measure an intracellular potential (Non-patent Document 3) which led to the development of rat myocardium. It has been reported that the intracellular potential of rat cardiomyocytes could be recorded successfully. However, in that method, the electrode loses access to the intracellular space, because the perforated cell membrane is repaired immediately. Therefore, it is not a practical method.

With the progress of intracellular recording methods, the development of extracellular recording methods for recording extracellular electrical changes has developed and become more widespread in recent years. The extracellular recording method, as represented by an in vitro multi-point planar electrode (multi-electrode array) system, records electrical changes extracellularly from electrodes placed outside the cell. (Patent Documents 1 to 4)

The application of the in vitro multi-point planar electrode (Multi Electrode Array, MEA) system began to be used in studies of plasticity of cultured nerve cells, or more specifically, drug safety testing using nerve cells and cardiomyocytes derived from human iPS cells.

Although MEA allows for easier handling of cells due to extracellular recording, this technology only allows recordings for AC-like changes (changes in membrane potential unit time, differential waveforms), so it is not applicable for recording slow changes in the intracellular membrane potential. Therefore, this measurement method does not provide sufficient information for analysis and its application is limited.

According to a report that attempted intracellular recording by a method based on MEA, cells were seeded on a mushroom-shaped electrode and high voltage was applied in order to break the cell membrane. The recording time of the intracellular potential could only be maintained for a short time, confirming it is not a practical recording method. (Non-Patent Document 1).

From the above, it is desired to provide a method for measuring intracellular potential having the following characteristics. It should be as stable and easy to handle as the MEA extracellular recording method, capable of high-precision recording equal to or higher than the manual patch clamp method, and applicable to membrane potential recording from a single cell in a cell culture (Non-Patent Document 4).

CITATION LIST

Patent Document

Patent Document 1: WO2012/043820
Patent Document 2: WO2013/061849
Patent Document 3: WO2014/098182
Patent Document 4: Japanese Translation of PCT International Application Publication No. 2005-505761

Non-Patent Document

Non-Patent Document 1: Anna Fendyur, et al., Frontiers in Neuroengineering, December 2011, Vol. 4, Article 14, p. 1-14
Non-Patent Document 2: Raphael Levy, et al., NanoReviews 2010, 1:4889-DOI: 10.3402/nano. v1i0.4889
Non-patent document 3: Micha E. Spira et al., Nature Nanotechnology Vol. 8 (February 2013) p. 83-94/DOI: 10.1038/NNANO.2012.265
Non-Patent Document 4: Khudhair D., et al., (2017) Emerging Trends in Neuro Engineering and Neural Computation. pp. 41-59

SUMMARY OF THE INVENTION

Problems to be Solved

The present invention aims at providing a method for accurately measuring the intracellular potential of a single cell unit or a cell population (sheet-shaped cells or cell clusters) by a simple method that is less invasive to cells and does not require a skilled procedure. In particular, the objective of the present invention is to provide a method capable of recording an action potential or a change in the action potential generated in a cell that cannot be cultured in a sheet, typically a cultured neuron.

Means for Solving the Problems

To measure the intracellular potential accurately, a glass microelectrode is inserted into the cell, the potential difference from the extracellular electrode (earth ground) is amplified through an amplifier, and the result is observed on a monitor.

In recent years, gold nanoparticles have been widely used not only as an immunodiagnostic kit but also as a delivery vehicle for nucleic acids and various drugs to mammalian cells including human cells, and the intracellular transfection method has a low burden on the cells is under development (Non-Patent Document 2). Moreover, the properties of gold nanoparticles are extremely low in cytotoxicity and highly electrically conductive. Because of the reasons described above, the present inventors have devised to use gold nanoparticles to introduce into cells instead of glass microelectrodes.

As a result of diligent research, the present inventors invented the methodology consists of the following steps; the test cells are cultured on a conductive glass plate then introducing the magnetic nanoparticles coated with gold into the cells. The gold nanoparticles are attracted to the magnet that is placed below the conductive glass plate, which then penetrates the cell membrane and forms a contact point between the inside of the cell and the conductive glass. One study examined the introduction of gold-coated magnetic nanoparticles into polyethyleneimine on cultured animal cells adhered to the surface of the conductive glass plate. The gold nanoparticles in the cells pulled towards the conductive glass plate surface by the magnet placed below, penetrated the cell membrane, and one end of the gold nanoparticles protruded outside of the cell and made contact with the conductive glass. The potential difference between the conductive glass that directly reflects the intracellular potential and the extracellular electrode (earth) is amplified by an amplifier. It was confirmed that the intracellular potential can be measured as in the case of using the conventional intracellular glass microelectrode.

An alternative method is to use a neodymium magnet placed above the cell as the magnet electrode. Neodymium magnets coated with a conductive metal are adhered from above the cells to generate a magnetic field. With the help of a magnetic force, conductive nanoparticles inside the cells (magnetic nanoparticles coated with gold) penetrates the cell membrane and contacts the magnet electrode MagEle. It was confirmed that the magnetic electrode functions as an intracellular recording electrode and the intracellular potential can be measured.

Therefore, by having a method of attracting the conductive nanoparticles and introducing them into the cells in advance by the magnetic field and penetrating the cell membrane, it was possible to connect the electrodes inside and outside the cells while minimizing damage to the cells as much as possible.

In addition, we have also developed a method for recording intracellular potentials that causes less damage to cells by penetrating the cell membrane from the outside of the cell because this method does not require the step of introducing conductive nanoparticles into the cell in advance. Specifically, a magnet electrode, in which conductive nanoparticles are adsorbed on the surface of the magnet electrode, is pressed against the cell surface from above the cell and is drawn to a metal plate provided below the cell to penetrate the cell membrane. It was confirmed that the magnet electrode and the intracellular recording electrode can be constructed by performing the above-mentioned series of operations.

It is possible to measure the intracellular potential by connecting the intracellular recording electrode constructed by these methods and the extracellular electrode (earth) provided in the extracellular fluid to an amplifier and amplifying the potential difference between both electrodes (The patent was filed on the same date).

The above method completed by the present inventors employs a method of penetrating the cell membrane with the conductive nanoparticles being pulled by the magnetic force, so that the method can be easily performed and damage to the cells can be suppressed as much as possible. This is an epoch-making technology that has a great merit making it possible to observe changes in intracellular potential while allowing cells to survive in a normal state for a long period of time. However, in terms of measuring the intracellular potential, that is, measuring the change in the potential difference between the intracellular potential and the extracellular potential in the extracellular fluid, this method is not significantly different from the conventional glass microelectrode method.

The present invention provides a method for measuring an intracellular potential using the principle of a capacitive charge amplifier, which is completely different from the conventional measuring method.

The present invention (capacitance type potential measuring device) is characterized in that a capacitor is used as a recording device in which one of the conductors forming the capacitor comes into contact with conductive nanoparticles (conductive nanoparticles, conductive peptides, etc.) penetrating the cell membrane. According to the method, change in charge between the two conductors forming a capacitor is recorded by connecting the above conductor to positive input and connecting another not being contact with cells to the negative input. Since the capacitance of the capacitor used in the capacitance type potential measurement device is small (<50 pF), the impedance (resistance) value of the capacitor is very high.

According to Ohm's law, a large potential difference occurs at both ends of a series circuit having a large impedance. It is known that the smaller the capacitance of a capacitor, the greater the impedance (capacitive reactance) (for example, http://www.fluke.com/fluke/uses/comunidad/fluke-news-plus/articlecategories/electrical/capacitivevoltage)).

From the above, when measuring the potential difference between both ends of a capacitor, by using a capacitor with a small capacitance, the resistance impedance between them becomes large, and it becomes possible to record a small potential change, such as the cell membrane potential.

In this case, the voltage amplifier acts as a "charge amplifier". That is, the flow of ions flowing into the cell through the cell membrane is recognized as a charge signal through the conductive nanoparticles penetrating the cell membrane. It is converted into a voltage signal change through a capacitor (charge-voltage converter) and measured by the voltage amplifier as a change in membrane potential.

Changes in intracellular potentials such as action potentials that occur within cells are caused by the movement of charged (Charge) ions ($Na^+$, $K^+$, $Ca^{2+}$, $Cl^-$) in and out of the cell. If this change in charged ion concentration is regarded as a change in charge through the conductive nanoparticles penetrating the cell membrane, it can be measured as voltage signals by applying the principle of a charge amplifier using a capacitance type potential measurement device.

That is, in the present invention, the "capacitive type potential measuring device" is a technique that enables direct current potential (voltage) measurement (intracellular membrane potential in the experimental example) to be performed without providing a ground in the measurement circuit. The feature is to use a capacitor with very high impedance and picofarad capacity. The potential change (charged ions entering and leaving the cell) that occurs at one end of the capacitor coupled to the conductive nanoparticle electrode is detected as a voltage because the high impedance capacitor acts as a charge-voltage converter (charge amplifier). The feature of this device is to connect the positive and negative inputs of the amplifier to both ends of the capacitor and measure the potential change directly. Since the negative pole in the device acts as the ground of the measurement circuit, it does not become an open circuit and enables stable measurement. Further, in the present invention, the "method utilizing the principle of charge amplifier" means that the change in the ion concentration in the cell due to the inflow and outflow of cations and anions through the cell membrane is perceived as a change in the charge through a conductive plate or other conductor that contacts the conductive nanoparticles that penetrate the cell membrane."

The measuring method of the present invention is significantly different from the existing intracellular or extracellular potential measuring methods. That is, instead of directly measuring the potential change occurring between the positive input (intracellular) of the amplifier and the negative input placed in the extracellular fluid, a capacitor (conductive plate) for seeding cells is used as a charge sensor to sense an electric charge, and the electric charge is converted into a voltage, which is recorded as a change in intracellular potential. Therefore, it is not necessary to set the earth in the extracellular fluid. The conductive plate, that is the sensor, only needs to be able to detect the change in the charge inside the cell through the conductive nanoparticles that penetrate the cell membrane. That means that the part of the conductive plate that is not covered with cells can be in direct contact with the extracellular solution. Therefore, it is particularly suitable for measuring the intracellular potential of a single cell such as a cultured nerve cell that cannot form into a cell sheet.

The present invention includes the following inventions.

[1] A capacitance type potential measurement device capable of recording intracellular potential or potential change of target cells, comprising: a conductive plate being in contact with an extracellularly exposed end of conductive nanoparticles penetrating the cell membrane of the target cells; and a magnet installed below a conductive sheet provided in contact with the lower surface of the conductive plate.

Here, as the conductive plate, in addition to conductive glass (glass with FTO (fluorine doped tin oxide), glass with ITO (indium doped tin oxide)), a titanium plate or the like is used. An aluminum foil, a silver plate, or a platinum plate is used as the conductive plate. Hereinafter, the same applies.

[2] The capacitance type potential measurement device according to [1], wherein the conductive plate is a conductive glass having a collagen-coated area on at least a part of its surface.

[3] The capacitance type potential measurement device according to [1] or [2], wherein the upper surface of the conductive plate is connected to the positive input of an electric signal amplifier, and the conductive sheet contacting the lower surface of the conductive plate is connected to the negative input of the electric signal amplifier, and a capacitive potential recording circuit is formed by the upper surface of the conductive plate and the conductive sheet.

[4] A capacitance type potential measurement device capable of recording intracellular potential or potential change of target cells, comprising: a magnet electrode being in contact with an extracellularly exposed end of conductive nanoparticles penetrating the cell membrane of the target cells, wherein the magnet electrode is fixed vertically and covered with insulator except for the lower surface to be in contact with the target cells; and a magnetic body or a magnet-attracting metal plate on the upper surface via the insulator, wherein the magnet-attracting metal plate is installed below the bottom surface of a container to which the target cells are adhered.

Here, as the insulator, parafilm, silicon, wax or the like is used but silicon tubes are preferred. The magnetic body may be the same material as the magnet electrode, and the magnet attracting metal plate is typically an iron plate. Hereinafter, the same applies.

[5] The capacitance type potential measurement device according to [4], wherein the insulator, covering the magnet electrode except for the lower surface being in contact with the target cells, is not entirely in contact with the lower substrate surface to which the target cells are adhered, and the target cells being in contact with the lower surface of the magnet electrode is not separated from extracellular fluid.

[6] The capacitance type potential measurement device according to [4] or [5], wherein the conductive nanoparticles penetrate the cell membrane by pressing the surface of the magnet electrode with pre-adsorbed conductive nanoparticles onto the target cells from above and by drawing the conductive nanoparticles to the metal sheet provided below the target cells to penetrate the cell membrane.

[7] The capacitance type potential measurement device according to [6], wherein the conductive nanoparticle pre-adsorbed on the surface of the magnet electrode is prepared using conductive nanoparticles pre-mixed with a transfection reagent.

[8] The capacitance type potential measurement device according to any one of [4] to [7], wherein the magnet electrode is connected to the positive input of the electric signal amplifier, and the magnetic body or the magnet-attracting metal plate provided on the upper surface of the magnet electrode via the insulator is connected to the negative input of the electric signal amplifier, and a capacitive potential recording circuit is formed by the magnet electrode and the magnetic body or the magnet-attracting metal plate.

[9] A method for measuring intracellular potential or potential change of target cells, comprising the following steps (1) to (3):
(1) introducing conductive nanoparticles into the target cells adhered on a conductive plate, wherein a conductive sheet is provided in contact with the lower surface of the conductive plate, and a magnet is provided below the conductive sheet;
(2) drawing the conductive nanoparticles in the target cells to the side of the surface to which the target cells are adhered, by a magnetic force derived from the magnet below the conductive plate, to penetrate the cell membrane of at least a part of the cell adhesive surface, and allowing an end of the conductive nanoparticle exposed to the outside of the target cells to be in contact with the conductive plate; and
(3) forming a potential recording circuit by connecting the upper surface of the conductive plate to the positive input of the electric signal amplifier and by connecting the conductive sheet to the negative input of the electric signal amplifier.

[10] A method for measuring intracellular potential or potential change of target cells, comprising the following steps (1) to (4):
(1) introducing conductive nanoparticles into the target cells adhered to the bottom surface of a container;
(2) adhering a magnet electrode to the upper surface of the target cells, wherein the magnet electrode is covered with insulator except for the surface to be adhered to the target cells, and a magnetic body or a magnet-attracting metal plate is provided on the upper surface of the magnet electrode via the insulator;
(3) providing the magnet-attracting metal plate below the bottom surface of the container to which the target cells are adhered, drawing the conductive nanoparticles to the side where the target cells are adhered to the magnet electrode, by a magnetic force generated between the magnet electrode and the magnet-attracting metal plate below to penetrate the cell membrane, and allowing an end of the conductive nanoparticle exposed to the outside of the target cells to be in contact with the magnet electrode; and
(4) forming a potential recording circuit by connecting the magnet electrode to the positive input of an electric signal amplifier and by connecting the upper magnetic body or the magnet-attracting metal plate to the negative input of the electric signal amplifier.

[11] A method for measuring intracellular potential or potential change of target cells, comprising the following steps (1) to (4):
(1) adsorbing conductive nanoparticles on the surface of a magnet electrode that is not covered with insulator;
(2) adhering and pressing the surface of the magnet electrode adsorbing the conductive nanoparticles onto the target cell surface from above the target cells, wherein a magnetic body or a magnet-attracting metal plate is provided on the upper surface of the magnet electrode via the insulator;
(3) providing the magnet-attracting metal plate below the bottom surface of a container that adheres to the target cells, drawing the conductive nanoparticles on the magnet electrode surface to inward direction of the target cells, by a magnetic force generated between the magnet electrode and the magnet-attracting metal plate below, and allowing the conductive nanoparticles to penetrate the cell membrane, leaving an extracellular end contacting the magnet electrode; and
(4) forming a potential recording circuit by connecting the magnet electrode to the positive input of the electric signal amplifier, and by connecting the magnetic body or the magnet-attracting metal plate to the negative input of the electric signal amplifier.

[12] A method for screening a substance having a toxic action or an activating action on target cells, comprising the following steps (1) to (6):

(1) introducing conductive nanoparticles into the target cells adhered on the conductive plate, wherein a conductive sheet is provided in contact with the lower surface of the conductive plate, and a magnet is provided below the conductive sheet;

(2) drawing the conductive nanoparticles in the target cells to the side of the surface to which the target cells are adhered, by a magnetic force derived from the magnet below the conductive plate, allowing the conductive nanoparticles to penetrate the cell membrane of at least a part of the cell adhesive surface, and making an end of the conductive nanoparticles exposed to the outside of the target cells be in contact with the conductive plate;

(3) measuring the voltage between the conductive plate and the conductive sheet, by connecting the upper surface of the conductive plate to the positive input of an electric signal amplifier, and by connecting the conductive sheet to the negative input of the electric signal amplifier to form a potential recording circuit;

(4) administering a test substance sample to the target cells;

(5) measuring the voltage between both electrodes, in the same manner as in step (3), of the target cells after the administration of the test substance sample in step (4); and (6) comparing the measurement result in step (5) with the measurement result in step (3), and evaluating the test substance sample as a substance having a toxic action or an activating action on the target cells if there is a significant difference between the two measured values.

[13] A method for screening a substance having a toxic action or an activating action on target cells, comprising the following steps (1) to (7):

(1) introducing conductive nanoparticles into the target cells adhered on the porous membrane of a cell culture insert;

Here, as the cell culture insert, a commercially available cell culture insert (Nunc Polycarbonate Cell Culture Inserts, Thermo Scientific) is preferable, and the bottom surface has a porous membrane of Polycarbonate. Those having a membrane pore size of 0.1 to 1.0 µm are preferable. Further, in order to carry out the perfusion of the solution from the lower surface of the cell, the cell is cultured on the porous membrane of the cell culture insert and is placed on the spacer, (2) adhering a magnet electrode to the upper surface of the target cells, wherein the magnet electrode is covered with insulator except for the surface to be adhered to the target cells, and a magnetic body or a magnet-attracting metal plate is provided on the upper surface of the magnet electrode via the insulator;

(3) providing a magnet-attracting metal plate below the porous membrane on the bottom surface of the cell culture insert to which the target cells are adhered, drawing the conductive nanoparticles to the side of the cell adhesive surface of the magnet electrode, by a magnetic force generated between the magnet electrode and the magnet-attracting metal plate below the porous membrane to penetrate the cell membrane, and allowing an end of the conductive nanoparticles exposed to the outside of the target cells to be in contact with the magnet electrode;

(4) measuring the voltage between the magnet electrode and the magnetic body or the magnet-attracting metal plate above, by connecting the magnet electrode to the positive input of an electric signal amplifier, and by connecting the magnetic body or the magnet-attracting metal plate above to the negative input of the electric signal amplifier to form a potential recording circuit;

(5) administering a test substance sample to the target cells through the permeable porous membrane of the bottom surface of the cell culture insert;

(6) measuring the voltage between both electrodes, in the same manner as in step (4), of the target cells after the administration of the test substance sample in step (5); and (7) comparing the measurement result in step (6) with the measurement result in step (4), and evaluating the test substance sample as a substance having a toxic action or an activating action on the target cells if there is a significant difference between the two measured values.

[14] A method for screening a substance having a toxic action or an activating action on target cells, comprising the following steps (1) to (7):

(1) adsorbing conductive nanoparticles on the surface of a magnet electrode that is not covered with insulator;

(2) adhering and pressing the surface of the magnet electrode adsorbing the conductive nanoparticles onto the target cell surface from above the target cells, wherein a magnetic body or a magnet-attracting metal plate is provided on the upper surface of the magnet electrode via the insulator;

(3) providing a magnet-attracting metal plate below the porous membrane on the bottom surface of a cell culture insert to which the target cells are adhered, drawing the conductive nanoparticles on the magnet electrode surface to inward direction of the target cells, by a magnetic force generated between the magnet electrode and the magnet-attracting metal plate to penetrate the cell membrane, leaving an extracellular end contacting the magnet electrode;

(4) measuring the voltage between the magnet electrode and the magnetic body or the magnet-attracting metal plate, by connecting the magnet electrode to the positive input of an electric signal amplifier, and by connecting the magnetic body or the magnet-attracting metal plate to the negative input of the electric signal amplifier to form a potential recording circuit;

(5) administering a test substance sample to the target cells through the permeable porous membrane of the bottom surface of the cell culture insert;

(6) measuring the voltage between both electrodes, in the same manner as in step (4), of the target cells after the administration of the test substance sample in step (5); and (7) comparing the measurement result in step (6) with the measurement result in step (4), and evaluating the test substance sample as a substance having a toxic action or an activating action on the target cells if there is a significant difference between the two measured values.

[15] A method for screening a substance having a toxic action or an activating action on target cells, comprising the following steps (1) to (6):

(1) introducing conductive nanoparticles into the target cells adhered on a substrate and adhering a magnet electrode to the upper surface of the target cells, wherein the magnet electrode is covered with insulator except for the surface to be adhered to the target cells, and a magnetic body or a magnet-attracting metal plate is provided on the upper surface of the magnet electrode via the insulator;

(2) providing a magnet-attracting metal plate below the substrate to which the target cells are adhered, drawing the conductive nanoparticles to the side of the cell adhesive surface of the magnet electrode, by a magnetic force generated between the magnet electrode and the magnet-attracting metal plate below to penetrate the cell membrane, and allowing an end of the conductive nanoparticles exposed outside of the cell to be in contact with the magnet electrode;

(3) measuring the voltage between the magnet electrode and the magnetic body or the magnet-attracting metal plate, by connecting the magnet electrode to the positive input of an electric signal amplifier, and by connecting the magnetic body or the magnet-attracting metal plate above to the negative input of the electric signal amplifier to form a potential recording circuit;

(4) administering a test substance sample to extracellular fluid and bringing the target cells into contact with the test substance sample, wherein the insulator covering the magnet electrode is not entirely in contact with the lower substrate surface to which the target cells are adhered, and the target cells being in contact with the lower surface of the magnet electrode is not separated from the extracellular fluid;

(5) measuring the voltage between both electrodes, in the same manner as in step (3), of the target cells after the administration of the test substance sample in step (4); and (6) comparing the measurement result in step (5) with the measurement result in step (3), and evaluating the test substance sample as a substance having a toxic action or an activating action on the target cells if there is a significant difference between the two measured values.

[16] A method for screening a substance having a toxic action or activating action on target cells, comprising the following steps (1) to (7):

(1) adsorbing conductive nanoparticles on the surface of a magnet electrode that is not covered with insulator;

(2) adhering and pressing the surface of the magnet electrode adsorbing with the conductive nanoparticles onto the target cell surface from above the target cells, wherein a magnetic body or a magnet-attracting metal plate is provided on the upper surface of the magnet electrode via the insulator;

(3) providing a magnet-attracting metal plate below the substrate on which the target cells are adhered, pulling the conductive nanoparticles on the magnet electrode surface to inward direction of the target cells, by a magnetic force generated between the magnet electrode and the magnet-attracting metal plate to penetrate the cell membrane, leaving an extracellular end contacting the magnet electrode;

(4) measuring the voltage between the magnet electrode and the magnetic body or the magnet-attracting metal plate, by connecting the magnet electrode to the positive input of an electric signal amplifier, and by connecting the magnetic body or the magnet-attracting metal plate to the negative input of the electric signal amplifier to form a potential recording circuit;

(5) administering a test substance sample to extracellular fluid and bringing the target cells into contact with the test substance sample, wherein the insulator covering the magnet electrode is not entirely in contact with the lower substrate surface to which the target cells are adhered, and the target cells being in contact with the lower surface of the magnet electrode is not separated from the extracellular fluid;

(6) measuring the voltage between both electrodes, in the same manner as in step (4), of the target cells after the administration of the test substance sample in step (5); and (7) comparing the measurement result in step (6) with the measurement result in step (4), and evaluating the test substance sample as a substance having a toxic action or an activating action on the target cells if there is a significant difference between the two measured values.

Effects of the Invention

In the present invention, since the conductive nanoparticles introduced into the cell by a known method or the conductive nanoparticles on the cell surface mixed with the transfection reagent are attracted by the magnetic field to penetrate the cell membrane, damage to the cells can be minimized as much as possible, and the fluctuation of the intracellular potential can be observed while allowing the cells to survive in a normal state for a long period of time.

In addition, the measuring method of the present invention does not directly measure the potential change between the positive input and the negative input of the amplifier, but this method of recording the change in intracellular potentials is performed using the charge-voltage conversion using a capacitor (conductive plate) that seeds cells as a sensor. Therefore, it is not necessary to set the earth in the extracellular fluid. Since it is sufficient that the conductive plate that serves as a sensor can sense a change in charge in the cell through the conductive nanoparticles penetrating the cell membrane, and the conductive plate may be in contact with the extracellular fluid at a portion not covered with cells.

That is, it is not necessary for the measuring method of the present invention to culture in a sheet form even when applied to a cell group, and even when applied to a single cell, the action potential of a cell or its change can be accurately measured easily.

Especially, even in cells that cannot be cultured in a sheet, typically in cultured nerve cells, it is possible to record the action potential generated in the cell or its change. Therefore, in the future, in vitro electrophysiology of (cultured) nerve cells, it is expected to make a dramatic contribution to scientific research.

Furthermore, by applying it to transformed cells or cell groups that express various ion channels, drug transporters, etc., it can be used as a tool for screening drug efficacy or cytotoxicity by observing changes in intracellular potential due to the addition of various drugs.

(D) illustrates a conceptual diagram showing the procedure by which gold-coated magnetic nanoparticles in cells are pulled towards the conductive glass surface by a magnet below the conductive glass surface.

Figure 2:
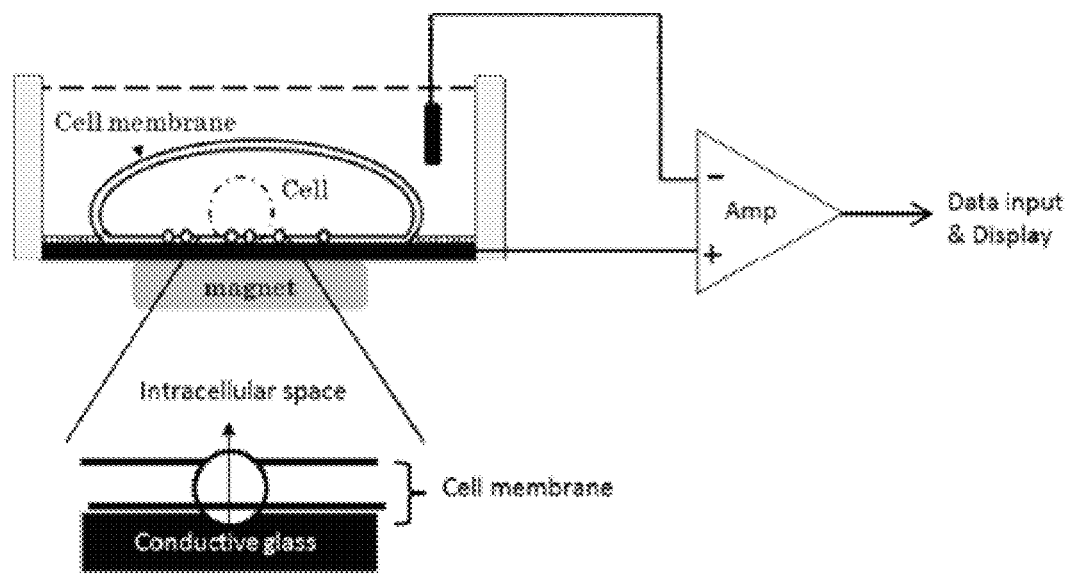

FIG. 2 illustrates a conceptual diagram showing that the intracellular potential is measured by extracellular devices of recording electrode, ground, and amplification amplifier.

Figure 3:
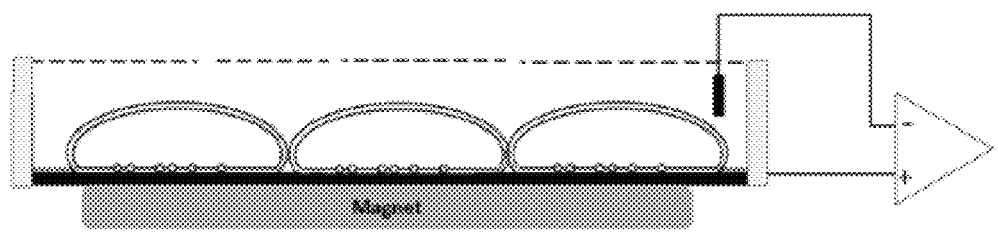

FIG. 3 illustrates a conceptual diagram showing that the intracellular potential is measured from a cell population seeded on the surface of a conductive plate.

Figure 4:
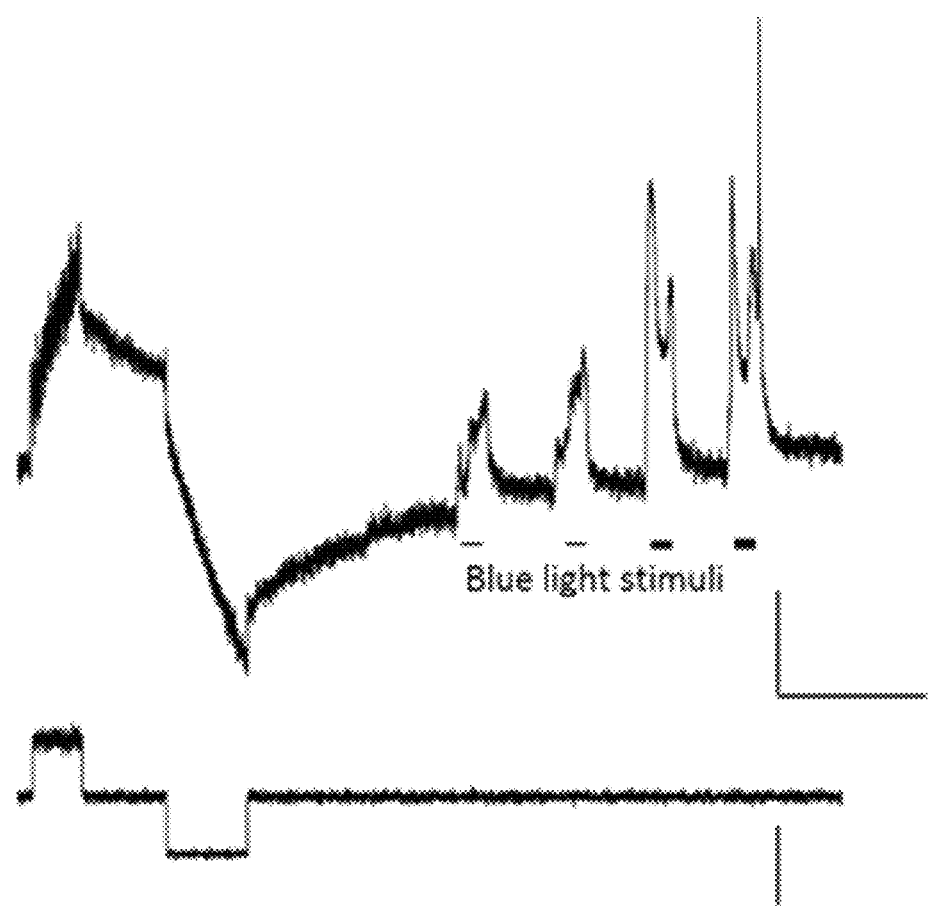

FIG. 4 illustrates a potential response to blue light stimulation on hChRWR expressing CHO cultured cells with gold-coated magnetic nanoparticle electrodes.

Figure 5:
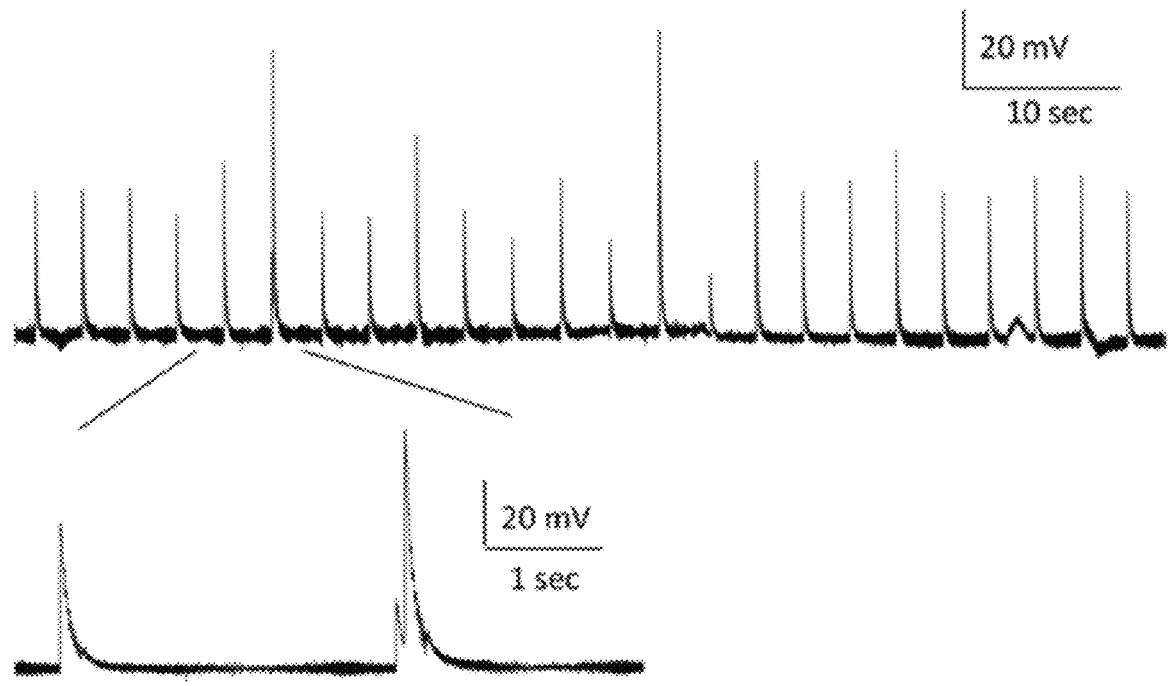

FIG. 5 illustrates a result of intracellular action potential measurement in Nav1.5/Kir2.1-expressing HEK cultured cells having gold-coated magnetic nanoparticle electrodes (Induction of action potential by membrane potential change).

Figure 6:
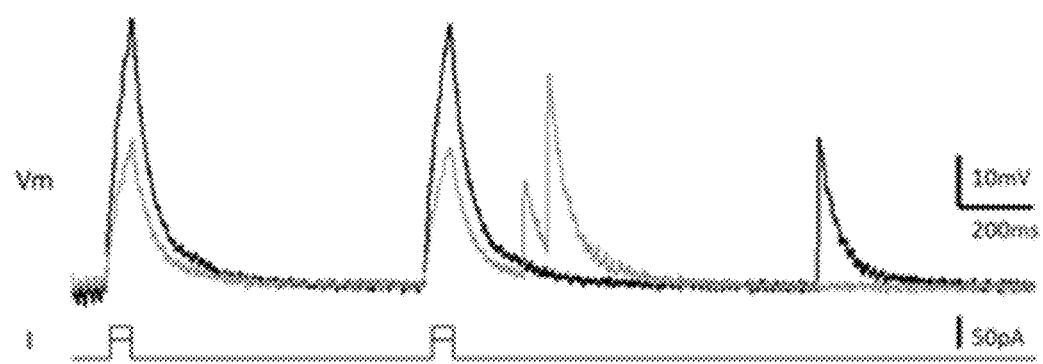

FIG. 6 illustrates a result of intracellular action potential measurement in Nav1.5/Kir2.1-expressing HEK cultured cells having gold-coated magnetic nanoparticle electrodes (Induction of action potential by the current pulse).

Figure 7:
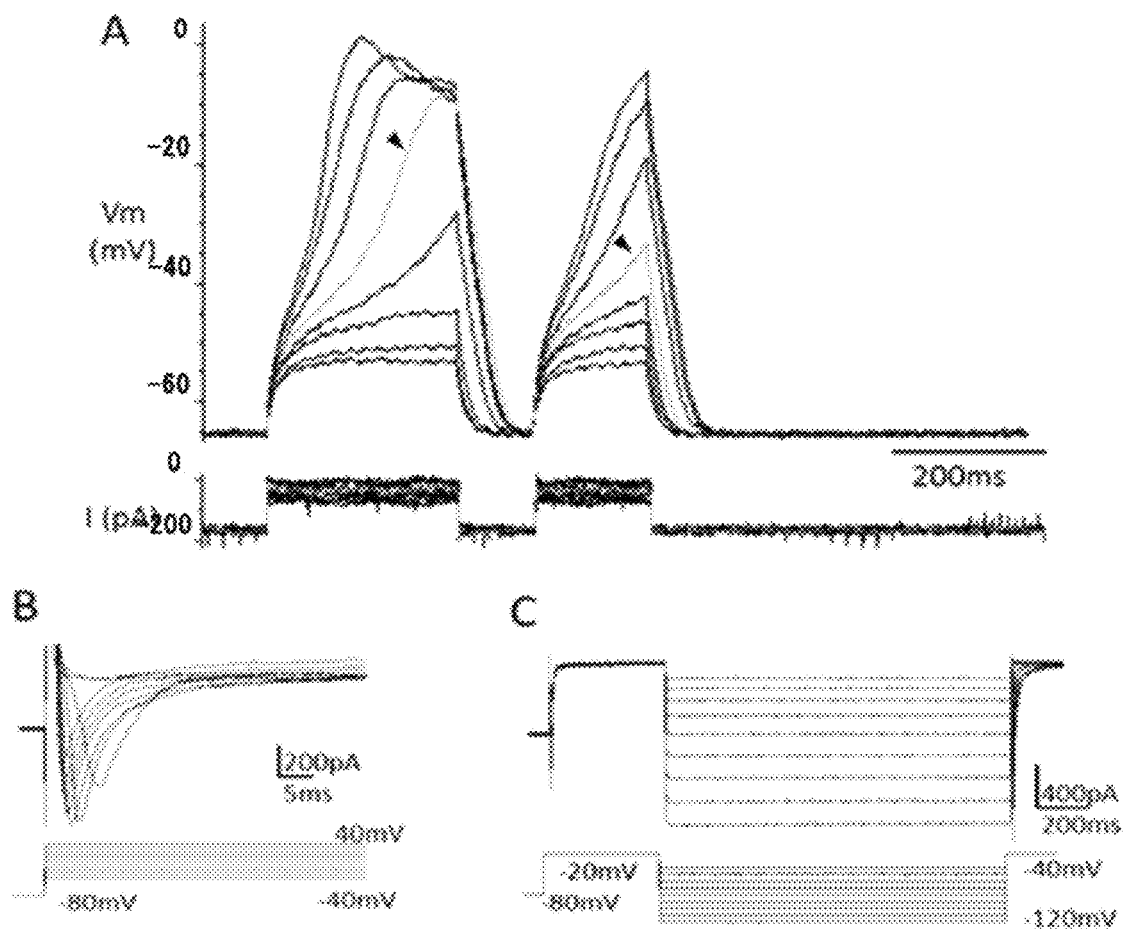

FIGS. 7(A) to (C) illustrate that action potentials recorded in Reference Example 2 are results of the expression of Nav1.5/Kir2.1 genes. Their functional expressions in HEK cells are verified using the Current-clamp method (FIG. 7(A)), and by the Voltage-clamp method, (FIGS. 7 (B) and (C)).

Figure 8:
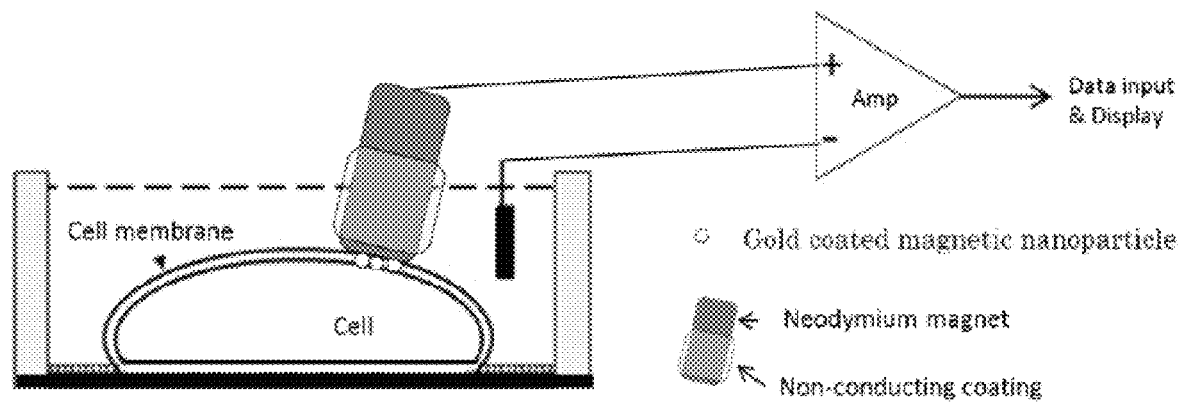

FIG. 8 illustrates a conceptual diagram showing that a neodymium magnet is used as a magnet electrode to allow gold-coated magnetic nanoparticles to penetrate the cell membrane and measure the intracellular potential. Since the magnet is much larger than the cells, the bottom surface of the magnet is attached to the surface of multiple cells.

Figure 9:
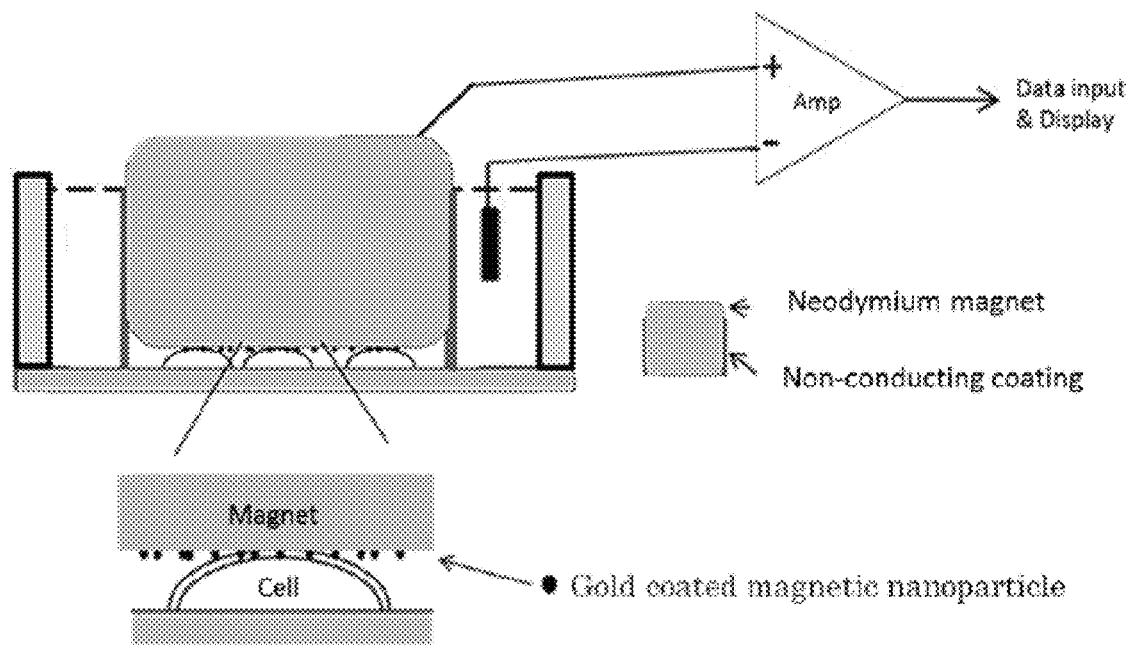

FIG. 9 illustrates a conceptual diagram showing the use of neodymium magnets to penetrate the cell membrane with gold-coated magnetic nanoparticles without introducing the nanoparticles into cells in advance.

Figure 10:
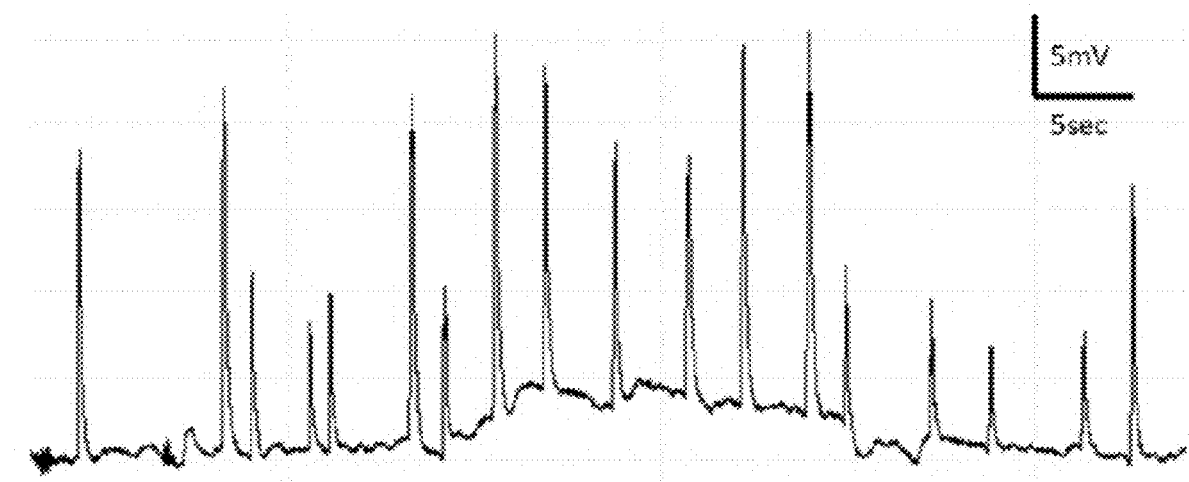

FIG. 10 illustrates a result of intracellular action potential measurement in Nav1.5/Kir2.1-expressing HEK cultured cells, with neodymium magnet electrode (induction of action potential by membrane potential change).

Figure 11:
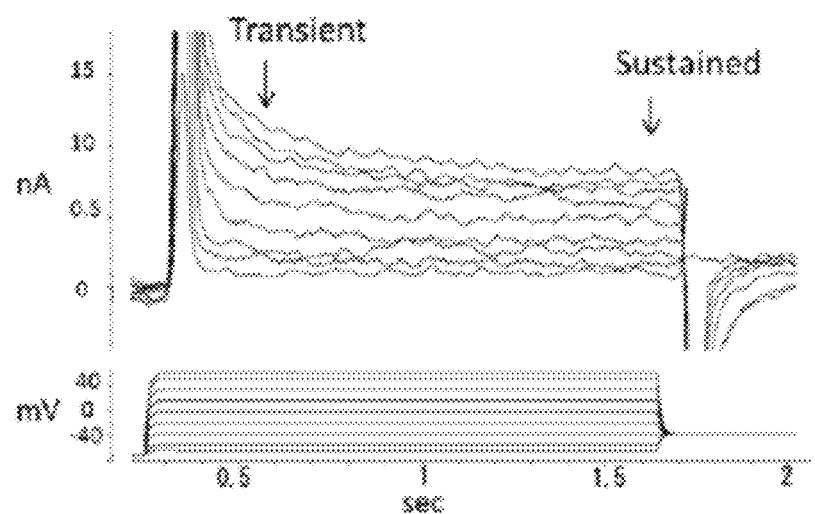
Figure 11:
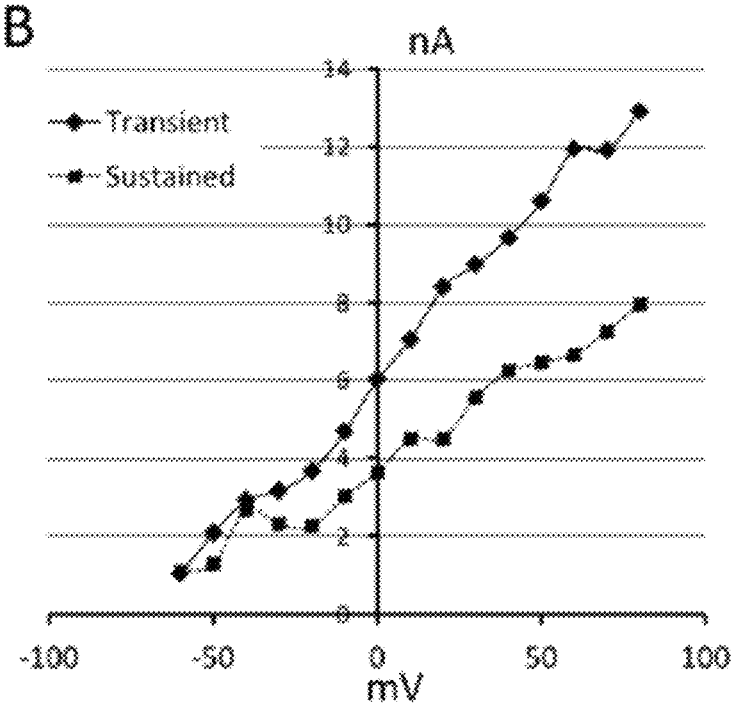

FIG. 11 illustrates a measurement of the endogenous outward current of CHO cells mediated by conductive nanoparticles penetrating the cell membrane of CHO cells cultured on a conductive plate electrode (by the voltage-clamp method).

Figure 12:
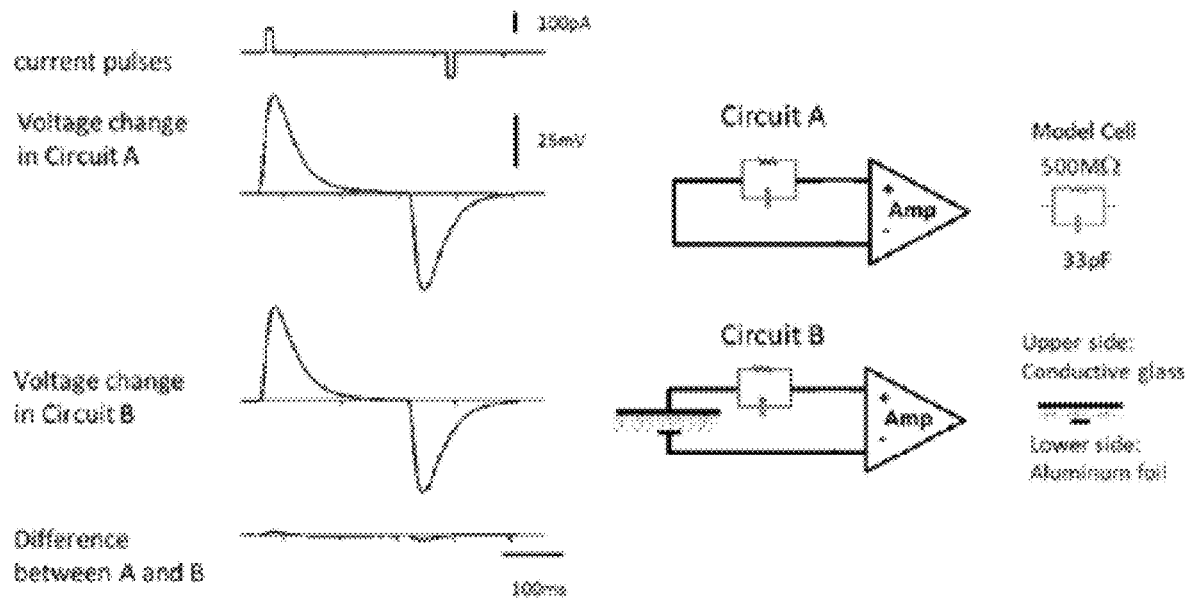

FIG. 12 illustrates a preliminary experiment of measuring the intracellular potentials based on the charge amplifier principle.

Figure 13:
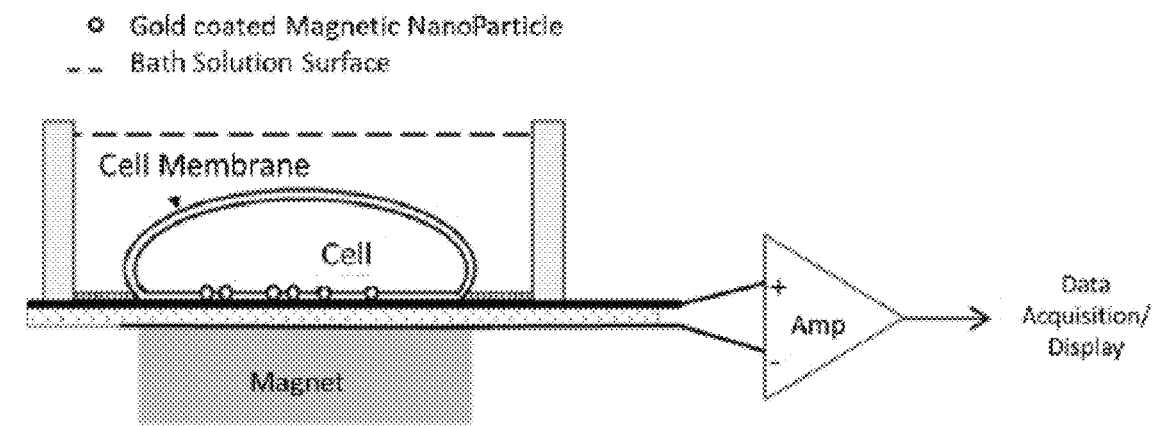

FIG. 13 illustrates a conceptual diagram showing that the intracellular potential (voltage) changes can be measured as detecting the changes in the charges by sing the principle of the charge amplifier.

Figure 14:
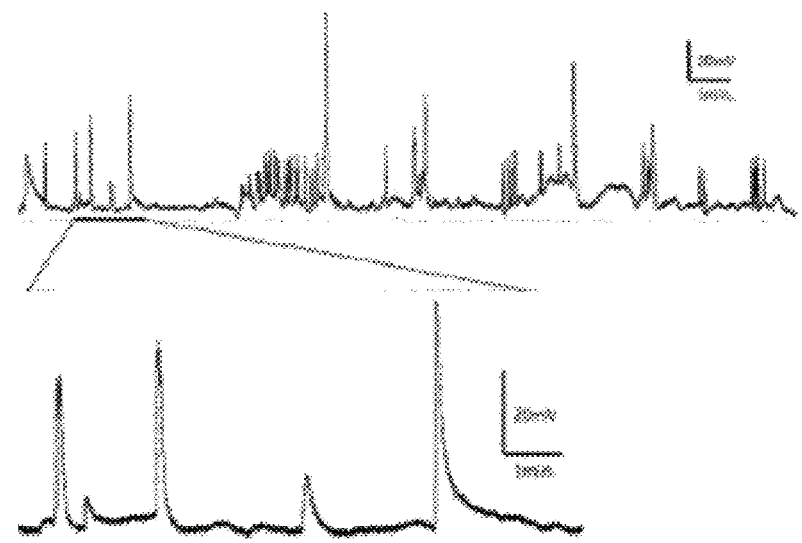

FIG. 14 illustrates recordings of Spontaneous Action Potentials from iPS Cell-Derived Cardiomyocyte Cells using intracellular Gold-Coated Magnetic Nanoparticle Electrodes introduced in advance based on the Principle of Charge Amplifier.

Figure 15:
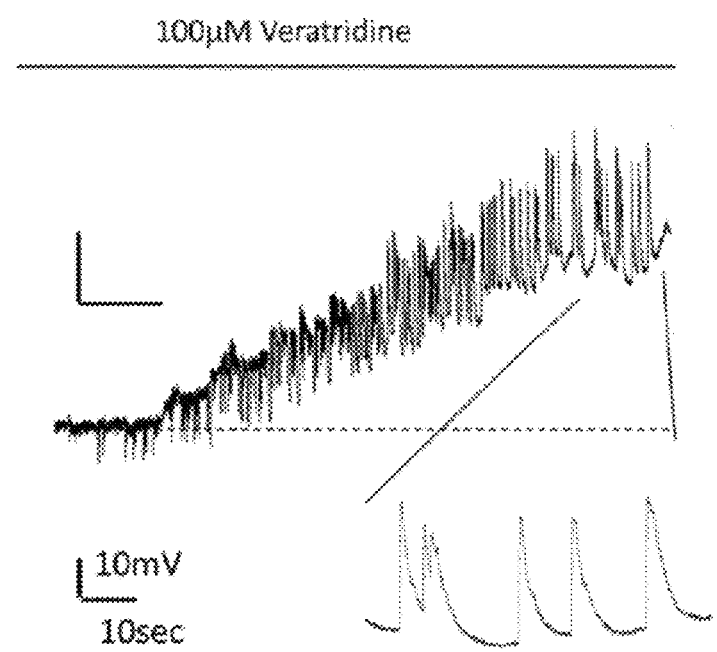

FIG. 15 illustrates the recording of sodium ion channel opener induced intracellular action potentials from cardiomyocytes cultured on a conductive glass surface coated with a collagen lattice, which was measured by detecting the changes in intracellular ion concentrations as changes in electric charge and then converting it into a change in voltage for measurement.

FIG. 16 (A) illustrates a conceptual diagram of a method recording the intracellular potential using the principle of the charge amplifier by using the conductive nanoparticles adsorbed on the magnet electrode as the intracellular electrode to penetrate the cell membrane instead of using conductive nanoparticles introduced into the cell in advance. A cover glass is used for cell culture.

FIG. 16 (B) illustrates a conceptual diagram of a method recording the intracellular potential using the principle of the charge amplifier by using the conductive nanoparticles adsorbed on the magnet electrode as the intracellular electrode that penetrates the cell membrane instead of using conductive nanoparticles introduced into the cell in advance. A cell culture insert is used for cell culture.

FIG. 17 (A) illustrates the experimental result for NG108-15 cells in which neural differentiation was performed for 5 days. Spontaneous action potentials were recorded by placing the magnet electrode, pre-adsorbed with conductive nanoparticles (C-M electrode), on cells seeded on coverslips.

FIG. 17 (B) illustrates the experimental result for NG108-15 cells in which neural differentiation was performed for 2 days. Glutamic acid was administered to the extracellular fluid (final external fluid concentration 800 $\mu$M), and the response mediated by glutamate receptors was recorded. The baseline and glutamate response artifacts in the figure were removed.

Figure 18:
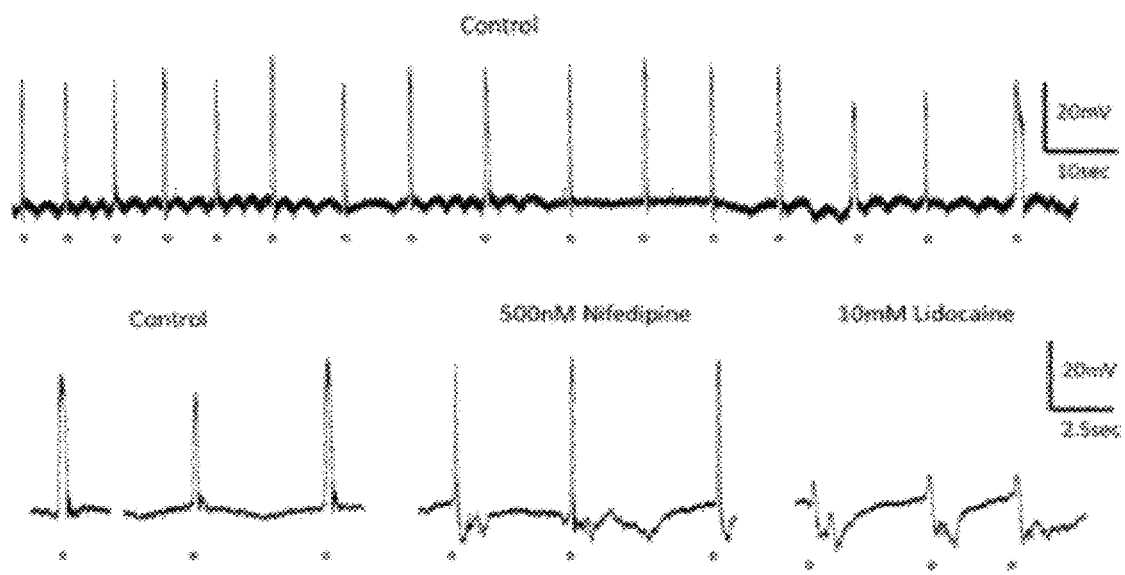

FIG. 18 illustrates a recording of intracellular potential in cells transiently expressing ion channels.

Figure 19:
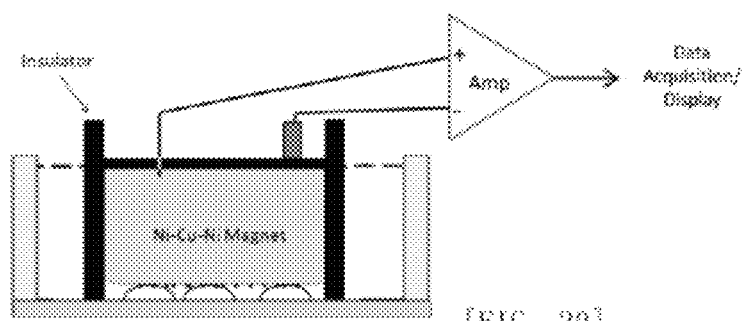
Figure 19:
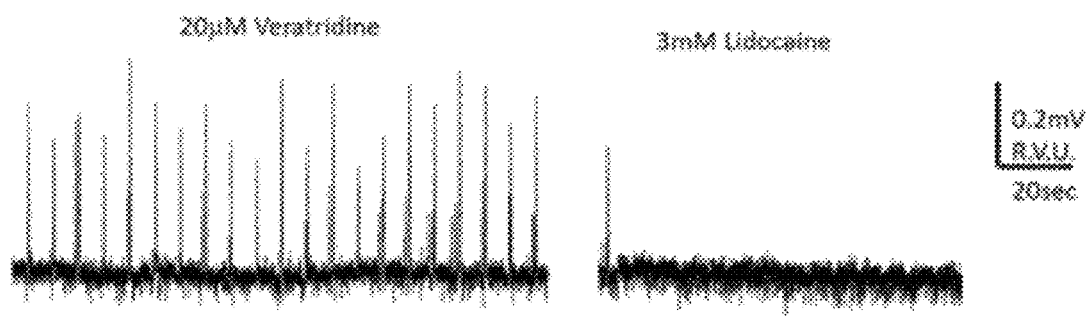

FIG. 19 illustrates a conceptual diagram showing that in the capacitive recording method in which the MagEle (magnet electrode) is fixed above the target cells, the external liquid flows in between the insulator on the side surface and the substrate.

FIG. 20 illustrates a recording of intracellular potential of differentiated cultured nerve cells (NG108-15 cells).

DESCRIPTION OF EMBODIMENTS

1. Conductive Nanoparticles Used in the Present Invention

In the present invention, "conductive nanoparticles" are nano-sized (25 to 100 nm) fine particles having both conductivity and magnetism. Generally used in the sense of "nanomagnetic particles coated with a conductive material", as long as it has the function of penetrating the cell membrane and acting as an electrode, its shape is not limited to a spherical shape, such as a linear shape, so other shapes may be used. Furthermore, the material may be nanoparticles having magnetism, conductivity, and low cytotoxicity, but conductive polymers, conductive peptides and the like can also be used.

As the conductive nanoparticles used in the present invention, it is common to use magnetic nanoparticles whose surface is coated with a material that is conductive and has almost no cytotoxicity.

Suitable materials for coating include, but not limited to, conductive metals such as gold and platinum (Yamada et al. (2015) WIREs Nanomed Nanobiotechnol 2015, 7:428-445. doi: 10.1002/wnan.1322), conductive peptides and proteins, or various conductive polymers. In the examples or reference examples described herein, citrate stabilized or PEG stabilized gold-coated magnetic nanoparticles (manufactured by nanoimmunotech, NITmagold Cit or PEG50 nm) are used. The gold-coated nanoparticles are mainly described herein as typical nanoparticles but are not limited thereto.

Further, as the core nanoparticles, any particles may be used as long as they have magnetism, but even if the particles are not coated, they can be similarly used as conductive nanoparticles as long as they are magnetic and electrically conductive, and also have low cytotoxicity.

Specifically, materials listed in the following documents can be used as the conductive polymer and the conductive peptides: "Poly(anthranilic acid) with magnetite nanoparticles achieves enhanced crystallinity, magnetic properties, and AC and DC conductivity" (Ramesan and Jayakrishnan, 2017, SPE Plastic Research On line 10.2417/spepro.006898). In addition, Quantum dot (Qdot) particles (00 Otelaja, D.-H. Ha, T. Ly, H. Zhang, and RD Robinson, "Highly Conductive Cu2-xS Nanoparticle Films, which have been conventionally used for staining of biological imaging through Room Temperature Processing and an Order of Magnitude Enhancement of Conductivity via Electrophoretic Deposition" ACS Applied Materials and Interfaces 6, 18911-18920 (2014)) and the like which have been conventionally used for staining biological imaging can also be used as the conductive nanoparticles.

The diameter (50 nm) of the conductive nanoparticles used in the present invention has the following requirements; because it needs to penetrate the cell membrane, so its diameter needs to be longer than the thickness of the cell membrane (about 20 nm), but in order to minimize damage to cells, the diameter should be as short as possible. That is, the most ideal numerical range is 40 to 60 nm but the ranges 25 to 100 nm, 30 to 80 nm, and 35 to 70 nm would all be acceptable. Commercially available gold-coated magnetic nanoparticles (Absolute Mag™ Gold Coated Magnetic Particles, Citrate diameter 50 nm, manufactured by Creative Diagnostics) (WHM-GC01), or the like may be used.

The conductive nanoparticles of the present invention may have other shapes, such as a linear shape, a spherical shape, a cylindrical shape, or a conical shape, as long as they have the function of penetrating the cell membrane and serving as an electrode. The maximum length of the particles is 25 to 100 nm, preferably 30 to 80 nm, and more preferably 35 to 70 nm, and even 40 to 60 nm would be preferred the most.

2. Cells to be Measured and Seeding of Cells
(2-1) Target Cell, Cell Population (Cell Group)

The cells to be measured in the present invention may be cells of biological origin such as cells collected by biopsy, or cultured cells. It is mainly intended for mammalian cells, such as humans, but may be eukaryotic microorganisms, such as yeast, prokaryotic microorganisms, such as *Escherichia coli*, as well as birds, fish, and insect cells.

In particular, cardiomyocytes, nerve cells, vascular epithelial cells, liver cells and the like, or cell populations thereof derived from human stem cells such as human iPS cells are preferred.

In addition, transformed cultured cells, that express various ion channel genes or transporter genes using mammalian cells such as HEK and CHO cells as transformation hosts, are preferred target cells in the present invention since it can be used as an evaluation system for a toxicity test of a drug incorporated from various ion channels or transporters.

The measurement target cell of the present invention may be a single cell, but in general, a cell population (cell group) that proliferates after cell culture or is formed during culture is targeted.

In the present invention, the term "cell population" refers to sheet-like cells formed on the surface of a culture dish (plate, well) for adherent culture, including cell clusters formed by cardiomyocytes, nerve cells, etc. derived from stem cells such as the iPS cells.

In addition, a target cell of the present invention includes an artificial cell containing a giant liposome which has been widely used as a model cell in recent years (Moscho et al. (1996) PNAS 93: 11443-11447; Schlesinger Saito (2006), Cell Death. and Differentiation 13, 1403-1408; Aimon et al. (2011) PLoS ONE 6(10): e25529. doi: 10.1371/journal.pone.0025529).

For example, a method of fusing a cell membrane fragment containing an ion channel separated from cells expressing an ion channel with a giant liposome, an artificial cell prepared by fusing a small liposome incorporating a recombinant ion channel protein expressed in *Escherichia coli* or the like with a huge liposome, can be used.

The present invention is particularly useful for drug discovery screening using model cardiomyocytes or nerve cells.

The following is the preferred cardiomyocyte model. Cardiomyocytes that have been induced to differentiate from stem cells, such as human iPS cells, or cells in which the cardiac muscle ion channel genes (SCN5A (Nav1.5), CACNα1C (Cav1.2), KCNH2 (hERG), KCNQ1/KCNE1 (LQT1), KCNJ2 (Kir2) 0.1)) have been introduced into cultured animal cells (HEK293, BHK, or CHO cells) and the above ion channels have been expressed in the cell membrane. As such cells, for example, myocardial model cells described in WO2014/192312 can be used.

Further, instead of the transformed cells, a cultured cardiomyocyte sample in which differentiation is induced from stem cells, such as iPS cells, can be used (U.S. Pat. No. 9,663,764B2; Generation of cardiomyocytes from human pluripotent stem cells). Myocardial iPS cells (iCell Cardiomyocytes) are also commercially available from CDI.

It is also possible to use a tissue section sample derived from a living body. At that time, as a tissue section, a myocardial section that forms atria or ventricles derived from mammalian cells was used to investigate the cause of atrial fibrillation and arrhythmia. A tissue piece or the like obtained by biopsy from the diseased tissue can be used.

For a nerve cell model, a photoreceptor channel expressing cell obtained by introducing a photoreceptor channel gene into a nerve cell differentiated from PC12 cells or cerebral cortex cells, or iPS cells, can be used by observing the potential response to photo-stimulation. After the addition of the test substance, it becomes possible to evaluate the cytotoxicity of the test substance to nerve cells and to evaluate the drug efficacy. The light-sensitive model nerve cells, channel opsin 2-expressing cerebral cortical nerve cells described in JP-A-2006-217866 can also be used.

Unlike cardiomyocytes, even if nerve cells cannot cover the entire surface of conductive glass with cells, the intracellular potential can be recorded by the method using the capacitance type potential measurement device of the present invention.

(2-2) Cell Seeding Method:

In the present invention, since the cultured cells do not need to cover the entire conductive plate recording area, it is not necessary for the cells to cover the entire conductive plate recording area when the conductive plate recording area has a sufficient number of cells for intracellular potential measurement. For example, it is preferable to sow 0.1-2.0×10$^5$ cells/cm$^2$, preferably 0.5-1.2×10$^5$ cells/cm$^2$. It is also possible to measure the intracellular potential in a single cell.

If a magnet electrode is used, the conductive plate area is not needed and a normal culture vessel or cover glass can be used, so a Polycarbonate cell culture insert (pore size 0.4 µm, Thermo Scientific) may be used. The number of seeded cells is not limited, but when the biopotential is measured using a cell population, it is also preferable to seed at a cell concentration of $0.1\text{-}2.0 \times 10^5$ cells/cm$^2$, preferably $0.5\text{-}1.2 \times 10^5$ cells/cm$^2$. It is also possible to measure the intracellular potential in a single cell, provided that the area of the magnet electrode other than the adhesion surface to the target cell is insulated and does not come into direct contact with the extracellular solution.

3. Method for Introducing Conductive Nanoparticles into Cells (3-1) Method of Introducing Conductive Nanoparticles into Target Cells Before Penetrating Cell Membrane In the present invention, there are two methods for penetrating the conductive nanoparticles into the cell membrane of the target cells by: a method of attracting conductive nanoparticles that have been previously introduced into cells by magnetic force towards the cell membrane from the inside to penetrate the cell membrane, and a method for penetrating the cell membrane by pressing extracellular nanoparticles against cells with magnetic force. This section describes a method used in the former case to previously introduce conductive nanoparticles into cells. The latter case will be described in detail in (4-3) below.

The method for introducing the conductive nanoparticles of the present invention into cells may be any of the methods described in the literature, which reviewed known methods for introducing nanoparticles into cells "Levy et al. (2010) Gold nanoparticles delivery in mammalian live cells: a critical review. Nano Reviews, 1: 4889-DOI: 10.3402/nano.v1i0.4889", either method is acceptable, but a method that minimizes damage to cells due to the introduction of nanoparticles is preferred. In Reference Example 1 and the like of the present specification, a polyethyleneimine solution (P3143 Sigma-Aldrich Mn ~60,000) is used as a transfection reagent, and Streptolysin O is used as a pore-forming protein toxin to the cell membrane. The method is not limited to the methods described above.

As a typical introduction method, for example, the following methods can be used, but are not limited thereto.

(3-2) A Method that Uses a Protein Toxin (Such as Streptolysin O) that Reversibly Forms Pores (Pathways that Penetrate the Membrane) on the Cell Membrane of Target Cells.

Protein toxins as pathogenic factors that form pores in the membrane of target cells have been known for a long time, and these protein toxins can be opened in reverse while controlling their toxicity to target cells. Technology that acts like a non-selective ion channel (pore) has also been developed (Walev et al., PNAS 98:(6) 3185-3190 (2001); T. Tomita., Bio. Soci. Japan General Incorporated. Association, Vol. 34, No. 6 (1994) p. 6-11).

As such a toxin, using streptolysin O of type A hemolytic *streptococcus* (Streptolysin O) and α-toxin of *staphylococcus* bound to liposomes are preferred. In Examples or Reference Examples described herein, examples using Streptolysin O are shown, but the present invention is not limited to Streptolysin O.

(3-3) Method Using Transfection Reagent:

As the transfection reagent, in addition to polyethyleneimine, Superfect (Qiagen) can be used, which is also known to make pores with dendrimer, similar to polyethyleneimine. Since polyethyleneimine has a large molecular weight, it forms a large pore, so it is more effective.

The transfection reagent is used as a typical reagent when introducing conductive nanoparticles into cells in advance, but it is also effective in the method (5) of allowing conductive nanoparticles to penetrate from outside the cell into the cell membrane.

(3-4) Method of Utilizing Intracellular Uptake by Endocytosis:

The difficulty with this method is that it requires a step of translocating from the endosome interior space to the cytoplasm after the conductive nanoparticles are taken up into the target cell.

For this purpose, it is preferable to add a cell penetrating peptide (CPP) such as TAT or TAT-HA to the conductive nanoparticles so as to transfer the cells from the endosome membrane to the cytoplasm.

(3-5) Method of Mechanically Inserting with a Shotgun (Genegun):

This method includes two methods: a method of introducing conductive nanoparticles into cells and then seeding target cells, and a method of inserting conductive nanoparticles after seeding target cells.

Either method may be used, but in the case of the former, there is an advantage that a commercially available device (HeliosR Gene Gun System, Bio-Rad) can be used; therefore, it is particularly suitable when a large number of cells and conductive nanoparticles are targeted.

4. Method for Penetrating Conductive Nanoparticles into the Cell Membrane of a Target Cell (4-1) Basic Principle of Conductive Nanoparticles Through Cell Membrane Used in the Present Invention (when Conductive Nanoparticles Preliminarily Introduced into Cell Penetrate Cell Membrane)

In the present invention, there are two methods for penetrating the conductive nanoparticles into the cell membrane of the target cells; a method of attracting conductive nanoparticles that have been previously introduced into cells by magnetic force towards the cell membrane from the inside to penetrate the cell membrane, and a method for penetrating the cell membrane by pressing extracellular nanoparticles against cells with magnetic force.

In either case, the basic principle of the present invention is that conductive nanoparticles previously introduced into cells are attracted to a magnetic field outside the cells to penetrate the cell membrane, so that the conductive nanoparticles are centered around the cell membrane, and one end is inside the cell and the other end is exposed outside the cell. As a result, the end of the conductive nanoparticle that is exposed senses changes in the charge inside the cell, since the change of the electric charge also occurs at another end exposed outside the cell, it is possible to measure and record the intracellular potential through the conductive plate electrode or the conductive magnet electrode in contact with the conductive nanoparticles exposed outside the cell. The conductive plate and magnet electrode work as a capacitor to detect electric charge as voltage. At that time, a conductive substance which functions as a connector for connecting the extracellular exposed portion of the conductive nanoparticles to the amplifier, and which constitutes an intracellular potential recording electrode together with the conductive nanoparticles is required. One of the electrodes made of such a conductive material is a conductive plate, and a cell potential measuring container in which at least a part of the bottom surface of a plate for seeding cells (usually also serving as a cell culture container) has conductivity, and a magnet is installed on the side opposite to the cell adhesion surface of the plate, the other is a "magnet electrode" (typically a neodymium magnet) with a conductive coating.

Hereinafter, a general method for using the conductive plate is described first, and then a case of using the magnet electrode is described.

(4-2) Procedure when Using Conductive Plate

Here, one embodiment in the case of applying to a cell population (cell sheet) will be described, but the method of the present invention is not limited to this.

(Step 1) Test cells are seeded on a culture dish or plate (hereinafter, simply referred to as a conductive plate) having at least a surface of conductivity, or a tissue section is brought into close contact with the surface of the conductive plate.

In the present invention, the "conductive plate" does not have to constitute the entire bottom surface of the culture container, and the conductive surface may be exposed to extracellular fluid. It can also be formed by conductive coating only the cell-adhesive surface of the glass surface of the culture dish using a conductive material. The conductive material for forming the conductive plate region, FTO (fluorine-doped tin oxide) or the like is preferably used, but the conductive material is not limited to this as long as the equivalent conditions are satisfied.

Here, it is preferable to use a transparent substrate, for example, a conductive glass, for seeding the cells, because the seeding state of the cells can be easily and accurately confirmed by a microscope. Although the conductive glass (manufactured by Kennis Co., Ltd.) is used in the examples or reference examples in the present specification, it is not limited thereto.

Further, as the conductive plate, a titanium plate used for culturing osteoblasts (Rosa and Beloti (2003) Effect of cpTi Surface Roughness on Human Bone Marrow Cell Attachment, Proliferation, and Differentiation. Braz Dent J 14(1): 16-21) and the like are also preferable. Titanium plate has almost no cytotoxicity and does not transmit light, but it has better conductivity than conductive glass, and since errors due to series resistance such as conductive glass (having an electrical resistance of 20-40 ohms) does not occur, a titanium plate or a non-toxic conductive metal is preferable when a particularly accurate measured value is required.

(Step 2) Nano-magnetic particles (particle diameter 25 to 100 nm) coated with a conductive material are introduced into cells. The "nanomagnetic particles coated with a conductive material" are also simply referred to as "conductive nanoparticles".

(Step 3) The conductive nanoparticles taken into the cells are attracted by a magnet (neodymium magnet, conductive magnet, etc.) placed below the culture dish to penetrate the lower side of the cell membrane.

(4-3) Reference: Procedures for Constructing Intracellular Recording Electrodes by Applying Gold-Coated Magnetic Nanoparticles to Single Cells (Conceptual Diagram)

A conceptual diagram when the method of the present invention using the conductive plate shown in (4-2) is applied to single cells of gold-coated magnetic nanoparticles, which are typical conductive nanoparticles of the present invention (FIG. 1 and FIG. 2), the procedure is as follows:

(1) Introduce gold-coated magnetic nanoparticles into cells (FIG. 1A-C).
(2) A magnet placed on the opposite side of the conductive glass to which cells are attached attracts the gold-coated magnetic nanoparticles to the conductive glass surface (FIG. 1D).
(3) Gold-coated magnetic nanoparticles attracted to the glass surface by the magnet penetrate the cell membrane of glass-adhesive part of cells.
(4) The gold-coated magnetic nanoparticles penetrating the cell membrane connect the electrodes to the inside of the cell, and the intracellular potential and current can be measured through the gold coating around the magnetic nanoparticles.
(5) The intracellular potential is measured by the recording electrode, the ground, and the amplification amplifier arranged as shown in (FIG. 2).

(4-4) Reference: Conceptual Diagram when Constructing an Intracellular Recording Electrode by Applying it to a Cultured Cell Population When applied to cultured cells in actual experiments, there are usually multiple cells. At that time, if contact between cells is not established, the glass surface that will be the electrode will be directly connected to the earth ground through the extracellular fluid (because of the ionized ions), which will short-circuit the gold-coated magnetic nanoparticles and the extracellular solution, and the intracellular potential through gold coated magnetic nanoparticles becomes not possible. For that purpose, it is necessary to spread the cells throughout the entire surface of the conductive plate (electrode) without any gap. It is desirable to make the electrode area as small as possible (FIG. 3). When a conductive material is drawn in a pattern on the surface of the culture dish to form the conductive plate area, the conductive plate area is formed so as to fit within at least the cell adhesion surface.

(4-5) Method Using Magnet Electrode (MagEle)

A magnet coated with a conductive material (for example, a conductive metal such as nickel or aluminum) can be used as a "magnet electrode (MagEle)" because it has conductivity as well as magnetic force. A typical one is a neodymium magnet.

The neodymium magnet has the highest magnetic force among the permanent magnets, but since it easily rusts, it is usually plated with nickel. Since a commercially available 1 mm diameter cylindrical neodymium magnet (Neomag Co., Ltd.) is also coated with Ni—Cu—Ni, it has a strong magnetic force, high conductivity and can be used as a magnet electrode (MagEle). Besides, it can be used as a magnet electrode (MagEle) even when it is coated with aluminum. Further, the magnet body may be any magnet as long as it can generate a magnetic field that can attract the conductive nanoparticles in the cell upward against the attractive force so is not limited to the neodymium magnet. An example using a different neodymium magnet will be described. The magnet may be placed on the cell or the cell may be placed on the magnet, as long as the nanoparticles introduced into the cell are attracted to the magnet electrode in contact with the cell.

More specifically, after introducing the conductive nanoparticles into the cells, the neodymium magnet is brought into contact with the cell membrane from above the cells in the solution, not from the culture dish side. The intracellular conductive nanoparticles are attracted to the upper side of the cell to penetrate the cell membrane. The reference drawing of FIG. 8 illustrates the example of how the intracellular recording electrode is constructed.

Since it is necessary to shield the extracellular solution completely from the neodymium magnet surface, except for the parts that come into contact with the cells, an insulating coat, such as silicone rubber or silicone tube, should be applied beforehand.

As described above, in the method of using the neodymium magnet as the magnet electrode (MagEle), it is not necessary to mount the cells on the conductive glass, and a normal culture dish can be used, so there is an advantage that the cells cultured in the culture dish can be used as they are and the change in the intracellular potential can be directly recorded after the nanomagnet particles are introduced.

As long as cultured cells or groups of cultured cells have sufficient contact area with the magnet electrode (MagEle) placed above it, cells do not need to be present in areas that do not come in contact with the MagEle. In other words, it is not necessary for the entire bottom surface of the dish to be covered with the cell population.

Since the magnet electrode builds an intracellular recording electrode with the conductive nanoparticles, the same procedure can be applied as when measuring the extracellular electrode (earth) and the intracellular potential.

In the present invention, to make the magnet electrodes function as capacitors themselves, the part of the magnet (covered with an insulating film) exposed from the extracellular fluid on the side opposite to the cell adhesion surface is connected to the negative electrode of the amplifier. Since the magnet electrode is coated with a conductive material, connecting it to the positive input of the amplifier establishes the same positional relationship as the recording method using the principle of the charge amplifier through the insulating film, so in this recording method, the extracellular fluid does not need to be grounded, as in the case of using the above-mentioned conductive plate.

(4-6) Method for Penetrating Conductive Nanoparticle from Outside the Cell Membrane Unlike the above-mentioned method, this method does not previously introduce the conductive nanoparticles into cells. This is a method in which the conductive nanoparticles that are magnetically adsorbed directly on the surface of the magnet electrode are pressed against the cells and are inserted into and penetrate the cell membrane by the magnetic force generated between the conductive nanoparticles and the metal plate placed on the opposite side.

More specifically, the conductive nanoparticles are fixed to the surface of the magnet electrode by the magnetic force. During this process, the conductive nanoparticles may be used in a state of being mixed with a transfection reagent typified by PEI (Polyethyleneimine). Subsequently, the magnet electrode is pressed against the surface of the target cell, and the magnetic force generated between the magnet electrode and the metal plate under the cell makes the magnet electrode self-supporting. When the magnet electrode is thin and the magnetic force is weak, it may be pressed against cells by a manipulator or the like without depending on the magnetic force of the lower metal plate. Nanoparticles adsorbed and immobilized on the surface of the magnet electrode are pressed against the cells and penetrate the cell membrane. As a result, an intracellular potential recording electrode is formed by the conductive nanoparticles having one end reaching the cytoplasm and the magnet electrode supporting the conductive nanoparticles.

In the process described above, when used in combination with a transfection reagent such as PEI, the introduction efficiency is further increased. It is highly possible that PEI or the like, which has properties similar to those of cell membrane lipids, attaches to the nanoparticles and assists cell membrane penetration. This method is an extremely non-invasive method because it is not necessary to introduce the conductive nanoparticles into the cytoplasm.

This method is also excellent when applied to cultured nerve cells in which cultured cells do not need to come into contact with each other because it is not necessary to install a ground in extracellular fluid as in the case of using a conductive plate.

The case of using PEI will be specifically described below, but other transfection reagents may be used, or the transfection reagent may be omitted.

Magnetic gold nanoparticles stabilized with PEG or citrate mixed with PEI are added to the magnet electrode, and the nanoparticles are magnetically adsorbed to the bottom part of the magnet electrode whose side is coated with an insulator.

More specifically, as the insulator, parafilm, silicon, wax, or the like can be used, all of the portions of the magnet electrode that come into contact with the extracellular fluid, except for the parts that come into contact with the nanoparticles, should be insulated. In the case of silicone, a silicone tube that tightly fits the magnet can be also used.

After about 30-minute incubation, the surface of the magnet electrode on which the conductive nanoparticles are adsorbed is faced downward, the magnet electrode is brought close to the cell in the culture container from above and brought into direct contact with the cell. Next, the culture container is placed on a material, such as an iron plate, in order to attract a magnet. The magnet electrode is fixed on the cell by being attracted to this iron plate, and the conductive nanoparticles penetrate the cell membrane by the action of PEI. At this time, since one end of the conductive nanoparticle is attached to the magnet electrode, it stays in the cell membrane and intracellular potential recording is performed from one end exposed in the cell. That is, intracellular potential recording can be achieved without introducing nanoparticles into cells in advance. However, in this method, if the magnet is too weak, the magnet electrode needs to be held to another manipulator, so it is necessary to optimize the strength and size of the magnet depending on the cell type and culture conditions.

5. Measuring Method of the Present Invention (5-1) Measurement Principle Applying the Concept of Charge Amplifier As described above, when the term "charge amplifier" is used in the present invention, the "charge amplifier" itself as the "charge amplifier" is not used, but the charge signal, which is a mechanism performed in the "charge amplifier", is converted into a voltage signal by way of using a charge-voltage converter for converting into changes and used as "the principle of the charge amplifier". "Using the principle of a charge amplifier" means "sensing changes in ion concentrations in a cell, through the conductive plate in contact with the conductive nanoparticles that penetrate the cell membrane, as changes in charges and converting it into voltage changes for measurement".

Changes in intracellular potentials such as action potentials that occur inside cells are caused by the movement of charged ions ($Na^+$, $K^+$, $Ca^{2+}$, $Cl^-$) in and out of the cell. If we consider it as the change of electric charge through the conductive nanoparticles penetrating through, it can be measured as a voltage signal by applying the principle of charge amplifier.

The amplifier used in the present invention often may be referred to as a "charge amplifier" for the sake of description, but the amplifier that is actually used is a normal patch clamp amplifier. By connecting a normal amplifier above and below the capacitor made of conductive glass when there is an ion in and out of the cells seeded on the conductive glass, since the ions are positively or negatively charged, it can be sensed as a charge movement and can be measured as a voltage. Since this mechanism acts as if it were a charge-voltage converter (charge amplifier), it is called the "principle of a charge amplifier (charge-voltage converter)" in the present invention.

This measurement principle is similar to the optical measurement method circuit for optical particles using photodiodes.

A conventional amplifier measures the current flowing between its positive and negative electrodes (earth), or the change in applied voltage (change occurring between electrodes). In the case of an optical sensor (photodiode), the photodiode senses a phenomenon (light intensity) outside the measurement circuit from the energy of photons (photon particles) and amplifies it as a change in electricity (voltage or current).

In the present invention, changes in the concentration of charged ions (e.g., $Na^+$, $K^+$, $Ca^{2+}$, $Cl^-$) flowing in or out of cells are regarded as changes in the amount of charge. It is detected by the charge sensor, that is composed of conductive nanoparticles and conductive plates. This is a method of measuring it as a voltage change. That is, in the present invention, charged ions are perceived and converted into electric changes, just as the photons perceived by the photodiode are converted into electric changes.

What differentiates the present invention from the conventional intracellular and extracellular potential recordings is that, instead of measuring the potential change between the positive and negative inputs of the amplifier, the capacitor (such as conductive plate) in which the cells are cultured is used as a detection sensor to measure the membrane potential by converting the charge into the voltage change.

Therefore, one of the major characteristics is that it is not necessary to set the earth ground in the extracellular fluid. This means that even if the conductive plate, which is the sensor, is in direct contact with the extracellular solution in the portion not covered with cells, the change in intracellular membrane potential can be measured as a change in charge. Due to this characteristic, intracellular recording can be performed even for cells that cannot be cultured in a sheet-like manner, such as nerve cells, unlike cardiomyocytes.

(5-2) Method for Measuring an Intracellular Potential with Conductive Nanoparticles Using the Principle of a Charge Amplifier with a Capacitance Type Potential Measurement Device in the Present Invention More specifically, for example, connect the upper surface of conductive glass seeded with cells, which is the input of the capacitance type potential measurement device, to the positive electrode, and connect the aluminum foil installed on the lower surface of the conductive glass (thickness 2 mm) to the ground as the negative electrode. At this time, the aluminum foil is placed between the lower surface of the conductive glass and the magnet. (Insulation tape may be placed between the aluminum foil and the magnet to prevent short circuiting the electrical circuit). A capacitor that functions as a capacitance type potential measurement device is formed by a conductive glass surface, a glass plate (having a conductive coating) that functions as a dielectric, and an aluminum foil. The conductive glass can be the same as in other conductive plates such as the titanium plate described in the above 4. (4-2) and the like, and the conductive plate of aluminum foil may be replaced by aluminum foil, and a silver plate, a platinum plate, or the like.

The action potential generated in the cell placed on the surface of the conductive glass is sensed as a charge, and the potential difference recognized above and below the capacitor can be measured as a voltage.

In addition, in order to control the intracellular potential in the target cells, it is necessary to employ a method of an electrical stimulation method (by using an electrical stimulation circuit having a ground separately from the capacitance type potential measurement device), or a light stimulation method (by expressing Channelrhodopsine gene etc.).

(5-3) Capacitive Recording Method for Setting Up MagEle (Magnet Electrode) Above the Target Cell In the conventional recording method described in detail in (4-5) above, the MagEle (magnet electrode, connected to the (+) pole) is fixed above the target cell, and the conductive nanoparticles adsorbed at the tip of the MagEle penetrate the cell membrane like an intracellular electrode to measure the intracellular potential. In order to install the ground (−) electrode in the external liquid, it is necessary to completely isolate the MagEle from the external liquid by the insulator provided on the side surface; therefore, the insulator must be pressed onto the substrate (culture plate, culture plate, etc.) without any gaps. (FIG. 9).

The term "substrate" used in the present invention includes all devices for adhering target cells for culturing, measuring and the like. For example, it indicates a culture dish, a culture plate, a conductive plate, or the like.

On the other hand, in the present invention (capacitive recording method), when MagEle (magnet electrode) is used (fixed above the target cell), the MagEle works as the (+) input. The top surface and side surfaces other than the contact surface with cells are completely covered with an insulator (such as a parafilm film). The magnetic body or the magnet attracting metal plate that serves as the ground (−) input is fixed above MagEle by sandwiching the insulating film. In the Clip-on Ground of the present invention, the MagEle and the insulating film covering the upper surface thereof acts as the capacitance of the capacitor. If a magnet-adsorbing iron plate or an alloy containing iron is used as the metal electrode, the (+) electrode and the (−) electrode can be integrated.

In that case, the lower surface of MagEle facing the target cell does not need to be isolated from the extracellular fluid. The insulator covered on the side surface of MagEle may be pressed onto the substrate without any gap as in the conventional case (FIG. 16A). It is also possible to allow the external fluid to diffuse and flow in without completely adhering to the substrate and not completely separating MagEle and the cells thereunder from the external fluid. (FIG. 19).

When using MagEle, it is desirable for the cell seeding density to be medium. The seeding density of the cells needs to be lower than that which are forming the sheet, as the composition of the extracellular fluid can be influenced by the electrical activity of the cells, especially if the surroundings are isolated. For example, when an action potential is generated, sodium ions flow into cells and potassium ions flow out of cells. When cells under MagEle are isolated from the external fluid, the extracellular sodium ions required for the generation of action potential become insufficient, which negatively affects the generation of action potential.

In the latter case where MagEle and the cells underneath are not isolated from the external fluid, MagEle detects changes in the intracellular charge that occur through the ion channels existing in the cell membrane, so that the concentration of ions around the cells is affected. Unless the exchange of ions inside and outside the cell to the extent that the ion concentration around the cell is affected, the part of MagEle that is in direct contact with the extracellular fluid is not affected by the external fluid, and only changes in intracellular potential due to ion channels on the cell membrane can be detected through conductive nanoparticles that penetrate the cell membrane. That is, the drug administered to the external fluid also diffuses and flows in, and it becomes possible to record the intracellular potential change when a drug is applied to cells.

The "Polycarbonate cell culture insert method" (FIG. 16B) is the most efficient method for causing the inflow of extracellular fluid.

In the "Polycarbonate cell culture insert method", the substrate to which cells are attached is a Polycarbonate permeable membrane with a pore size of 0.4 µm (Thermo Scientific), and since the inflow of the external liquid through the gap below the insert occurs smoothly, the intracellular potential change due to the drug to be administered can be efficiently observed.

6. Method for Detecting Intracellular Potential or its Change (Present Invention) and Device for the Measurement (Conventional Type)

(6-1) Container for the Intracellular Potential Measurement

In the present invention, when using a magnet electrode, a general-purpose culture dish or culture plate can be used as it is as a culture container for seeding and culturing target cells. Also, even when a conductive plate is used, it can be used as a culture container because the conductive plate region is provided on at least a part of the bottom surface of the culture container for direct culture. Therefore, in any case, the culture container used for seeding and culturing the target cell can be used as it is as a container for measuring intracellular potential. Then, if necessary, it is possible to transfer from the container used for culture to another container for measuring intracellular potential, which is easier to measure.

When using the culture container, as it is as a container for measuring intracellular potential, the conductive nanoparticles are introduced into the target cells in the culture vessel. Then, the culture solution was washed with physiological saline several times and replaced with physiological saline. Immediately, a magnetic field attracts the conductive nanoparticles inside the cell to the side of the magnet electrode or the conductive plate to penetrate the cell membrane, whereby the intracellular potential or potential change can be measured and recorded.

In the method using the principle of the charge amplifier, it is not necessary to completely cover the bottom surface in the form of a sheet regardless of whether the conductive glass is used or the magnet electrode is used. For the purpose of the experiment, a buffer solution having a different ionic composition can be used instead of physiological saline as long as the osmotic pressure and pH are maintained.

(6-2) Use of Device (Conventional Type) for Measuring Intracellular Potential

In the present invention, the spontaneous potential in the cell and the induced potential, the intracellular potential is detected by the conductive nanoparticles penetrating the cell membrane, transmitted through the conductive plate electrode or the magnet electrode, and recorded by a device outside the cell. Since the potential change that occurs at that time is weak, a device equipped with a voltage amplifier (amplification amplifier) is essential for recording the intracellular potential.

As such an instrument, any instrument conventionally used for measuring the intracellular potential or the extracellular potential of a cell or a group of cells can be used.

More specifically, as the patch clamp amplifier intracellular recording amplifier, an amplifier having an input resistance of at least $10^6$ to $10^8$ ohms or more can be used. For example, a patch clamp amplifier (Axopatch 200A, Axon instruments) or the like can be used.

Further, the MEA system can be used as long as it can measure a DC signal instead of an AC signal.

7. Application of the Present Invention (7-1) Drug Discovery Screening

The present invention is particularly useful for drug discovery screening.

Alternative to conventional patch clamp method or auto patch method, the intracellular potential measurement method of the present invention can record the action potential and resting membrane potential of a cell using a measurement method utilizing the principle of a charge amplifier.

In drug discovery screening, by using the above model cardiomyocytes and model nerve cells, it is effective for evaluating the test substance by evaluating the cytotoxicity and drug efficacy of the test substance, since it is possible to quickly and accurately analyze the influence of the test substance on cell function, contractile activity by electrical stimulation, and analysis of changes in electrophysiological characteristics.

(7-2) Method for Recording Ligand Gated Receptor Ion Channels

Among the present invention, as an example of applying a capacitance type potential measurement device using a magnet electrode to a screening method, a procedure for screening a substance having a toxic action or an activating action on a ligand receptor activated ion channel-expressing cell is described. Although shown below, the procedure is not limited to the following.

More specifically, the following steps (1) to (6) are performed according to the procedure.

(1) A step of introducing conductive nanoparticles into target cells adhered on the porous membrane of a cell culture insert.

As the porous membrane, commercially available cell culture inserts (Nunc Polycarbonate Cell Culture Inserts, Thermo Scientific) can be used, and those having a porous membrane of Polycarbonate having a pore size of 0.1 to 1.0 µm. Particularly preferably 0.4 µm is used. Alternatively, Millicell inserts (Merkmillipore), cell culture inserts from Fisher scientific, Corning can also be used.

In addition, in order to perfuse the solution on the lower surface of the cell, a step of culturing the cell on the porous membrane and setting it on the spacer is required.

(2) A step of adhering a magnet electrode to the upper surface of the target cells.

In this step, the magnet electrode is covered with an insulator except for the adhesion surface to the target cells, and has a magnetic body or a magnet adsorbing metal plate on top of the magnet electrode covered with insulation.

(3) A step of providing a magnet-attracting metal plate below the porous membrane on the bottom surface of the cell culture insert to which the target cells are adhered, drawing the conductive nanoparticles to the side of the cell adhesive surface of the magnet electrode, by a magnetic force generated between the magnet electrode and the magnet-attracting metal plate below to penetrate the cell membrane, and allowing an end of the conductive nanoparticles exposed to the outside of the target cells to be in contact with the magnet electrode.

Although there is a gap of about 3 mm between the bottom of the cell culture insert and the magnet attracting metal plate, the impact of the gap on the experiment is small and need not be considered.

(4) A step for measuring the voltage between the magnet electrode and the magnetic body or the magnet-attracting metal plate above, by connecting the magnet electrode to the positive input of an electric signal amplifier, and by connecting the magnetic body or the magnet-attracting metal plate above to the negative electrode of the electric signal amplifier to form a potential recording circuit.

(5) A step of administering a test substance sample to the target cells through the permeable porous membrane (Polycarbonate membrane, pore size 0.4 μm) of the bottom surface of the cell culture insert.

(6) A step of measuring the voltage between both electrodes, in the same manner as in step (4), of the target cells after the administration of the test substance sample in step (5).

(7) A step of comparing the measurement result in step (6) with the measurement result in step (4), and evaluating the test substance sample as a substance having a toxic action or an activating action on the target cells if there is a significant difference between the two measured values.

EXAMPLES

The present invention will be specifically described below with reference to Examples, but the present invention is not limited to these.

Other terms and concepts in the present invention are based on the meanings of terms commonly used in the art, and various techniques used for carrying out the present invention are notably defined as those demonstrating the source thereof. Except for this, those skilled in the art can easily and surely carry out the implementation based on publicly known documents and the like. In addition, various analyzes and the like were carried out by applying methods described in analytical instruments or reagents used, instruction manuals of kits, catalogs and the like.

The description in the technical documents, patent publications, and patent application specifications cited in this specification shall be referred to as the description of the present invention.

(Reference Example 1) Measurement of Intracellular Potential in CHO Cells Stably Expressing Photoreceptor Channel (ChRWR)

In this reference example, using a normal patch clamp amplifier (Axopatch 200A, Axon instruments) as a device for intracellular recording, according to the intracellular potential recording method of the present invention, the intracellular potential of CHO cells expressing a photoreceptor channel (Channelrhodopsin: ChRWR) is measured.

(1-1) Generation of hChRWR-CHO Stable Expressing Cell Line

Photoreceptor channel (ChRWR) is said to have a 7-transmembrane rhodopsin-like structure and is known to respond upward (depolarization) to 480 nm blue light stimulation.

Yao and his group (Wang et al.) constructed a chimeric gene, Channelrhodopsin (ChR)-wide receiver (ChRWR), from ChR1 and ChR2, and used the ChRWR gene to highly express ChR2 (Channel rhodopsin 2) in the cell membranes of PC12 cultured cells and cerebral cortical nerve cells. It was confirmed that the response of intracellular potential by light stimulation could be recorded by the patch clamp method, and the authors reported that photosensitivity can be imparted to nerve cells. (Wang et al., 2009, J. of Biol. Chem. 284(9): 5685-5696, and JP 2006-217866 A).

In this reference example, the ChRWR gene (1073 bp) provided by Prof. Yao was used and amplified by PCR using Phusion DNA polymerase with the following primers.

Sense primer: CACTATAGGGAAGCTaccatggctcggagaccctggct (SEQ ID NO: 1)

Antisense primer: ATAGAATAGGAAGCTCTActtgcctgtccctttgttga (SEQ ID NO: 2)

The obtained PCR product was cloned into the pD603 (puromycin, DNA2.0) vector using the InFusion HD Cloning kit (Takara Bio) to construct an hChRWR expression vector. This hChRWR expression vector was introduced into CHO cells (JCRB cell bank) (Superfect, Qiagen) to generate CHO cells stably expressing the hChRWR gene (hChRWR-CHO stable expression cell line).

Figure 1:
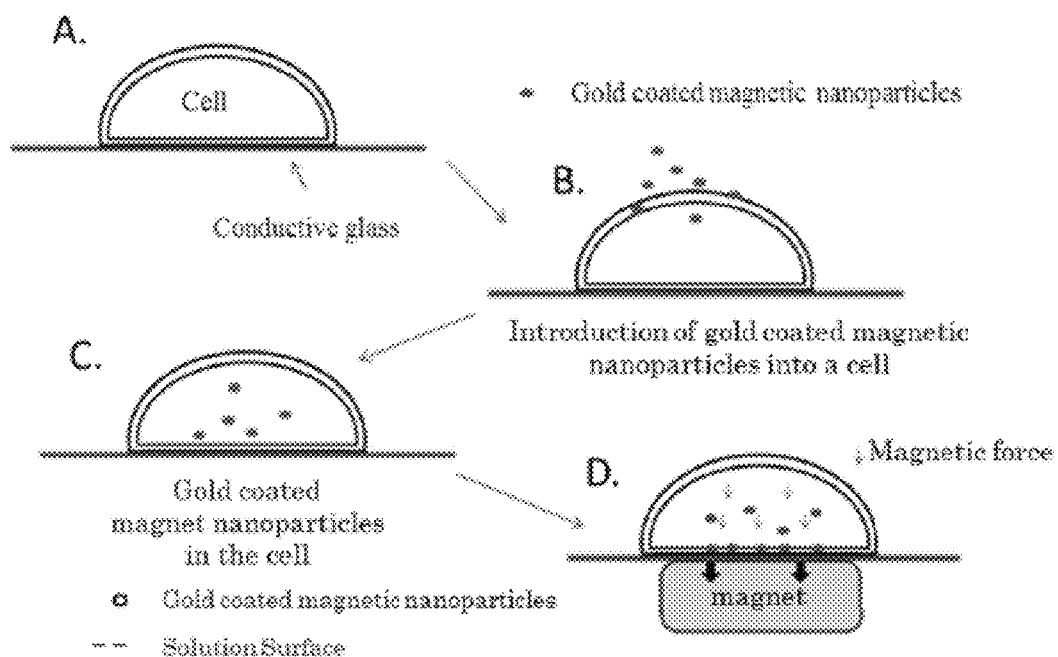
FIGS. 1 (A) to (C) illustrate a procedure for introducing gold-coated magnetic nanoparticles into cells, and FIG. 1

(1-2) Construction of Intracellular Recording Electrode Using Gold-Coated Magnetic Nanoparticles As a process of forming an intracellular electrode with gold-coated magnetic nanoparticles, the gold-coated magnetic nanoparticles introduced into cells are pulled by a magnet from below to penetrate the cell membrane. As a result, the gold-coated magnetic nanoparticles are exposed partially inside and outside the cell at the same time by spanning through the cell membrane. Since the cells are seeded on the extracellular recording electrode, when the gold-coated magnetic nanoparticles penetrate the cell membrane, they act as intracellular recording electrodes (FIG. 1).

The introduction of gold-coated magnetic nanoparticles into CHO cells was carried out by using Polyethyleneimine (PEI, P3143 Sigma-Aldrich) with a protocol improved based on the following URL (Https://labs.fccc.edu/yen/docs/PEI%20preparation.pdf).

More specifically, a 10 mg/ml PEI solution (pH 7) was prepared in advance, and the solution in which undissolved PEI has been removed using a 0.2 μm filter (Minisart, Sartorius stedim) was stored at −80° C. Immediately before use, only the used portion was diluted 100 times with ddH$_2$O before use. 5 μl of PEI diluted solution was added to 80 μl of gold-coated magnetic nanoparticles and 20 μl of 5×HBPS (24 mM HEPES+126 mM NaCl, 4 mM KCl, 1 mM CaCl$_2$, 1 mM MgCl$_2$, 10 mM Glucose) mixture and incubated at room temperature for 15 minutes.

Then, the cultured hChRWR-CHO cells prepared in the above (1-1) were washed with serum-free DMEM (Sigma-Aldrich) or OptiMEM I (Invitrogen)-containing buffer (PBS). Then the above solution was replaced with a solution containing gold-coated magnetic nanoparticles and incubated for 15 minutes in an incubator at 37° C.

Next, by applying a magnet from below the conductive glass to which the above-mentioned cultured cells adhere, when the conductive nanoparticles penetrate the cell membrane, the intracellular potential is detected, and one end of the nanoparticle exposed outside the cell comes into contact with the conductive glass to form an intracellular recording electrode capable of recording the intracellular potential.

The intracellular potential of cells on conductive glass is measured by a device consisting of recording electrodes, grounds, and amplification amplifiers arranged as shown in FIG. 2. The culture was performed so that the cultured cells would be tightly packed in a narrow area (circular area with a diameter of 1.5-2 mm) on the glass surface so that the cells would not directly short-circuit with the extracellular fluid.

(1-3) Measurement of Intracellular Potential with Gold-Coated Magnetic Nanoparticle Electrode The cultured cells having the intracellular recording electrode constructed in the above (1-2) were irradiated with blue light to measure the response amount to the light stimulation.

Blue light stimuli (irradiation for 12 seconds) were applied every 25 seconds, and the output intensity of blue light was increased in four levels (Max 1.2A, LED Driver M00290257, 470 nm M470F1, Thorlabs).

Increasing the blue light output from left to right also resulted in an increase in the upward potential response (depolarization) (FIG. 4).

From this result, gold-coated magnetic nanoparticles introduced into the cells, seeded on the extracellular recording electrode. can penetrate the cell membrane and be connected to the electrode. It was confirmed that the intracellular membrane potential can be measured by a patch clamp amplifier (Current-clamp mode, Axopatch 200A, Axon instruments) which is a cell membrane potential recording device.

Further, in the present invention, unlike the conventional cell non-invasive intracellular potential measurement method, a stable electrical response could be recorded for at least 30 minutes without being attenuated.

(Reference Example 2) Measurement of Intracellular Potential in HEK Cells Stably Expressing Nav1.5/Kir2.1

In this reference example, intracellular potentials are measured using HEK cells that stably express Nav1.5/Kir2.1 that spontaneously generate action potentials.
(2-1) Generation of HEK Cells Stably Expressing Nav1.5/Kir2.1

HEK cells (JCRB cell bank) were transfected with the Nav1.5/Kir2.1 gene to establish HEK cells that stably express Nav1.5/Kir2.1.

More specifically, first, the human Na+ channel α subunit (Nav1.5) was excised from a cDNA clone (SCNAS, BC140813: Source Bioscience) and inserted into pcDNA3.1 (−) hygromycin (Invitrogen).

Since BC140813 is the Embryonic type Nav1.5 gene, the adult type Nav1.5 gene was created by replacing the Embryonic type exons with the adult type exons by the PCR method using human heart cDNA (Zymogen).

The Kir2.1 (NM_000891, KCNJ2) gene (1284 bp) was subjected to the nesting PCR method using the following primers to total RNA extracted from iPS cell-derived cardiomyocytes (CDI, Cellular Dynamics International).

Kir2.1 1st sense: CCAAAGCAGAAGCACTGGAG (SEQ ID NO: 3)
Kir2.1 1st A/S: CTTTGAAACCATTGTGCTTGCC (SEQ ID NO: 4)

The Kir2.1 gene was obtained by performing a second PCR using the product diluted 100-fold from the first PCR as a template.

Kir2.1 ICR HindIII sense: CACTATAGGGAAGCTACC atgggcagtgtgcgaaccaac (SEQ ID NO: 5)
Kir2.1 ICR HindIII A/S: ATAGAATAGGAAGCT tcatatctccgactctcgccg (SEQ ID NO: 6)

The obtained Kir2.1 PCR product was inserted into the HindIII site of pD608 (blasticidin, DNA2.0).

The Nav1.5 gene (50 ug/ml hygromycin) and Kir2.1 gene (Kir2.1 2 ug/ml blasticidin) were introduced into HEK293 cells (Culture solution, DMEM, Sigma-Aldrich, 10% FBS) to obtain a stable Nav1.5/Kir2.1 expression cell line.
(2-2) Measurement of Intracellular Potential Then, HEK cells were cultured (DMEM, Sigma-Aldrich, 10% FBS), and as in Reference Example 1, when almost the entire glass surface was covered by HEK cells, gold-coated magnetic nanoparticles in a PEI diluted solution were introduced into the HEK cells and incubated at 37° C. for 15 minutes on the measurement glass surface, and a magnet was applied from the lower surface of the measurement glass to bring the gold-coated magnetic nanoparticles into contact with the measurement glass to construct an intracellular recording electrode.

As a result of recording intracellular potential, it was possible to stably record the action potential as a change in membrane potential amplitude in the range from 60 mV to 80 mV (FIG. 5).

Similarly, changes in intracellular potential due to action potential induced by applying current pulse could also be recorded (FIG. 6).

(Reference Example 3) Electrophysiological Evaluation of Nav1.5/Kir2.1 HEK Cells In this reference example, using the patch clamp method, HEK cells stably expressing Nav1.5/Kir2.1 used in Reference Example 2 were electrophysiologically evaluated to verify the method of the present invention.

The composition of extracellular fluid and intracellular fluid used is as follows.

Extracellular fluid: 126 mM NaCl, 4 mM KCl, 1.8 mM $CaCl_2$), 1 mM $MgCl_2$, 24 mM HEPES, 10 mM Glucose (pH7.4 NaOH)
Intracellular fluid: 130 mM KCl, 5 mM $MgCl_2$, 5 mM EGTA, 4 mM Tris-ATP, 10 mM HEPES (pH7.2 KOH)
(3-1) Verification Using the Current-Clamp Method HEK cells stably expressing Nav1.5/Kir2.1 used in Reference Example 2 were stimulated by current injection, and intracellular action potential-like changes in membrane potential were recorded (FIG. 7A). In the figure, the upper trace (Vm) shows the change in membrane potential, and the lower trace (I) shows the amount of applied current. When the amount of acting current was increased stepwise, in addition to the passive membrane potential response, a self-regenerative potential (action potential) was generated according to the all-or-none law due to Nav1.5 activity. Nav1.5 activity kinetics has the property that inactivation occurs immediately after activation. And, Nav1.5 activity stays low during the recovery phase from the inactivated state (refractory period). As shown by the arrow head, the response to the second electrical stimulation is significantly reduced compared to the response to the first electrical stimulation. This strongly suggests that the self-regenerative (action) potential is a Nav1.5-mediated potential response (FIG. 7A).
(3-2) Verification Using Voltage-Clamp
<Nav1.5 Current (FIG. 7B)>

The membrane potential was held at −80 mV (Holding potential), and the potential was changed from −40 mV to 40 mV in 10 mV increment from the membrane potential. Along with this, a transient inward sodium current due to Nav1.5 activity was recorded (FIG. 7B).
<KCNJ2 (Kir2.1) Current (FIG. 7C)>

The membrane potential is fixed at −80 mV as in the Nav1.5 current measurement of FIG. 7B. First, change the membrane potential to −20 mV so that the Kir2.1 current can be easily measured (a transient Nav1.5 current can be confirmed immediately after). This −20 mV pulse inactivates Nav1.5 and makes Kir2.1 current easier to observe. From there, the existence of the Kir2.1 current was confirmed by hyperpolarizing the membrane potential by −10 mV from −40 mV to −120 mV. Furthermore, by stepping the membrane potential to −20 mV, the steady-state inactivation properties of Nav1.5 current were also examined.

According to the above-mentioned verification by the patch clamp method, the cells used in Reference Example 2 are cells that can stably express Nav1.5 and Kir2.1. It was confirmed that the measured value in Reference Example 2 was a measured value of action potential based on Nav1.5/Kir2.1 expression. This indicates that the present invention enables intracellular potential measurement similar to the conventional patch clamp method with a simpler operation.

(Reference Example 4) a Method of Introducing Conductive Nanoparticles Using a Method of Making a Hole in a Cell Membrane with a Protein Toxin In this reference example, gold-coated magnetic nanoparticles were introduced into cultured cells using Streptolysin O according to a modified method of Walev et al. (PNAS 98:(6) 3185-3190 (2001)) described below.

First, Streptolysin O (SLO) (manufactured by Wako Pure Chemical Industries, Ltd.) was reduced and activated using DTT. Then, the SLO concentration was adjusted to about 5 U/μl.

Then, $2.5 \times 10^6$ of CHO or HEK cells were mixed with 40 μl of gold-coated magnetic nanoparticles and a gold-coated magnetic nanoparticle transfer solution (20 μl 5×HBPS (1 mM $Ca^{2+}$, 1 mM $Mg^2$1, 80 μl dd$H_2$O) and mixed with SLO. Then this mixture was incubated for 10 minutes at 37° C. From this process, pores were formed in the cell membrane by SLO, and at the same time, the gold-coated magnetic nanoparticles were transferred (introduced) into the cells through the pores.

SLO pore inactivation (closing) was completed by mixing 500-1000 μl of cell-containing solution with DMEM 10% FBS and incubating at 37° C. for 20 minutes or longer. A large number of gold-coated magnetic nanoparticles were introduced into the cells. Presence of nanoparticles aggregates were confirmed under a microscope.

From the above, it was confirmed that the conductive nanoparticles can be introduced into cells even by the method using the protein toxin.

(Reference Example 5) a Method of Using a Magnet Electrode (MagEle), which Utilizes the High Conductivity of a Neodymium Magnet (5-1) Method of attracting conductive nanoparticles inside cells with magnet electrode. In this reference example, an intracellular recording electrode is constructed by using a 1-mm diameter cylindrical neodymium magnet (Neomag Co., Ltd.) coated with Ni—Cu—Ni as a neodymium magnet electrode (MagEle).

Using "Nav1.5/Kir2.1 stably expressing HEK cells" prepared in Reference Example 2, the neodymium magnet electrode (MagEle) above the cell attracts the gold-coated magnetic nanoparticles previously introduced into the cell to the magnet electrode, penetrates the cell membrane to construct an intracellular recording electrode, and records intracellular potential changes. (FIG. 8).

More specifically, "HEK cells stably expressing Nav1.5/Kir2.1" prepared in Reference Example 2 were cultured in a normal culture medium (DMEM, Sigma-Aldrich, 10% FBS).

As described in Reference Example 1, gold-coated magnetic nanoparticles were introduced into cells using a PEI diluted solution. For introducing nanoparticles, SLO may be used as in Reference Example 4. By attracting the gold-coated magnetic nanoparticles introduced into the cells with the neodymium magnet electrode (MagEle) placed above the cells. The intracellular recording electrode was constructed by penetrating the cell membrane with gold-coated magnetic nanoparticles, and intracellular potential changes were recorded (FIG. 10).

(5-2) Method of Penetrating Conductive Nanoparticle Adsorbed on Magnet Electrode into Cell Membrane Gold-coated magnetic nanoparticles (NITmagold Cit manufactured by nanoimmunotech) mixed with PEI were added to the surface of the magnet electrode coated with an insulator on the side surface, and the nanoparticles were adsorbed to the magnet electrode over about 30 minutes.

From above Nav1.5/Kir2.1 HEK cells and cultured cardiomyocyte (iCell cardiomyocyte) in a culture dish placed on an iron plate, the magnet electrodes were directly contacted with the adsorption surface of the conductive nanoparticles facing downward. It was observed that the magnet electrode was attracted to the iron plate below the culture dish and fixed above the cells, and the conductive nanoparticles penetrated the cell membrane by the action of PEI and remained inside the cell membrane due to the magnetic force from the magnet (FIG. 9).

Furthermore, in any cell, the intracellular potential change could be recorded by the obtained intracellular recording electrode as in the case of (5-1).

That is, an intracellular recording electrode based on a magnet electrode having adsorbed a mixture of conductive nanoparticles and PEI can be constructed without the step of previously introducing conductive nanoparticles into cells. By pressing this electrode against the cell, it was confirmed that the intracellular potential change can be recorded with very low invasiveness.

(Reference Example 6) Cell Seeding Method for Cells with Weak Adhesion to Conductive Glass Surface Normal animal cells such as CHO cells efficiently adhere to the conductive glass surface, but some cells such as cardiomyocytes and HEK cells have extremely low adhesion efficiency to the conductive glass surface. When such cells are directly seeded on the surface of the conductive glass, it is extremely difficult to culture the cells to cover the entire surface of the conductive glass forming the bottom surface of the culture vessel.

Therefore, collagen is applied to the surface of the conductive glass in a grid shape in advance, and cells are seeded on the conductive glass with collagen grid shape coating and cultured until the entire surface is covered. In the place where the collagen coating film is not present, the conductive nanoparticles penetrating the cell membrane can be directly contacted with the conductive glass.

Although collagen has a low conductivity, it has a high cell adhesion property and a high adhesion property to the conductive glass, so that it is possible to improve the cell adhesion rate at the collagen coating film portion. Other examples of such substances include fibronectin and Poly-L-lycine, which can be used in place of collagen.

(Reference Example 7) Measurement of the CHO Cell Endogenous Outward Current by Conductive Nanoparticles Penetrating the Cell Membrane of CHO Cells Cultured on Conductive Plate Electrode Using the Voltage Clamp Method In this reference example, by using the intracellular recording electrode constructed by the conductive plate electrode and the conductive nanoparticles inside the cell, it was confirmed that the cell membrane current generated in the cell as well as the intracellular potential can be measured.

CHO cells were cultured in a culture medium containing Minimum Essential Medium Eagle (Sigma-Aldrich), 10% FBS (BioWest), 40 mM L-Glutamine (Wako Pure Chemical), and Streptolysin O (SLO) (manufactured by Wako Pure Chemical Industries, Ltd.) was reduced using DTT to prepare activated SLO at a concentration of about 5 U/μl.

CHO cells ($5×10^5$) were suspended in gold-coated magnetic nanoparticle transfection solution (5 μl 5×HBPS (1 mM $Ca^{2+}$, 1 mM $Mg^{2+}$)) containing 20 μl of gold-coated magnetic nanoparticles and were cultured on conductive glass. When CHO cells were grown to cover the entire glass surface, cell membrane currents were recorded using the voltage clamp method with gold coated magnetic nanoparticle electrodes. Before the experiment, replace the CHO culture solution (Minimum Essential Medium Eagle Sigma-Aldrich, 10% FBS BioWest, 40 mM L-glutamine Wako Pure Chemical) with the extracellular solution (24 mM HEPES+ 126 mM NaCl, 4 mM KCl, 1 mM $CaCl_2$, 1 mM $MgCl_2$, 10 mM Glucose). The voltage clamp experiment was performed using Axopatch 1D (Axon Instruments) using the headstage (CV-4) used for the experiment of the artificial lipid membrane. The reason is that in order to control the membrane potential by the voltage clamp method, it is necessary to first charge the capacitance derived from the lipid membrane of all cell membranes on the conductive glass. In this experiment, since hundreds of cells were cultured on the conductive glass, the capacity increased in proportion to the number of cells. Therefore, an amplifier capable of supplying a large current is essential. Because of that, a Voltage clamp Amplifier that can instantly flow a large amount of current is required.

In the experiments using the Voltage clamp method, the membrane potential was held at −80 mV, and 1.4 seconds long voltage steps of −60, −50, −30, −10, 10, 30, 50, and 60 mV were applied (FIG. 11A lower part). An outward current was observed in response to the stimulation of the membrane potential (FIG. 11A upper). The amplitudes of the Transient and Sustained currents were measured at each of the points indicated by arrows in FIG. 11A, and in FIG. 11B, and the current-voltage relation were plotted in the graph (Current (vertical axis, nA) and voltage (horizontal axis, mV).

A supplementary explanation will be given of the method for measuring the membrane current used for this experiment and the equipment therefor.

A patch clamp amplifier is used to measure the membrane current (current flowing through an ion channel existing in the cell membrane) in the Voltage clamp mode is used instead of the Current clamp mode used for recording the cell membrane potential. When controlling the membrane potential of many cells at the same time instead of a single cell, since the membrane capacity of the entire cell membrane (lipid bilayer membrane) is the number of cells×the capacity derived from the lipid bilayer membrane per cell, it becomes very large. Therefore, unlike the case of Reference Example 1 and the like, an Axopatch-1D Patch-clamp amplifier (Axon Instruments) capable of flowing a large amount of current is used.

The Axopatch 200A (Voltage clamp) used in the above Examples or Reference Examples is particularly suitable for the usual experiment for controlling the membrane potential of a single cell. When recording from a large number of cells, due to the large total cell membrane-lipid bilayer membrane, it is therefore necessary to compensate the large cell membrane-derived capacitance to control membrane voltage. Therefore, the Axopatch-1D amplifier was employed for this experiment since it can be used with the CV-4 Head stage developed for an experimental measurement of artificial lipid bilayer membranes with large membrane capacitance. Since the head stage for the artificial lipid bilayer membrane can record a large current, it has an advantage that the lipid bilayer membrane of many cells can be charged quickly. In addition, Bilayer Clamp Amplifier (BC-535) (Warner Instruments) etc. may be used in place of Axopatch-1D Patch-clamp amplifier.

(Example 1) Method of Measuring by Applying the Principle of Charge Amplifier (1-1) Preliminary Experiment for Applying the Principle of Charge Amplifier This experiment is an experiment to show that the measurement system is effective in measuring biopotential by combining a charge amplifier with nanoparticles introduced into cells (FIG. 12).

Circuit A shows a circuit in which a current-clamp mode patch clamp amplifier Axopatch 200A used for recording and a model cell (cell equivalent circuit: a circuit in which a 500 MΩ resistor and a 33 pF capacitor are connected in parallel) are connected. Two rectangular current pulses of different polarities (20 ms, 120 pA) separated by 250 ms were applied to this circuit, and the potential change through the circuit A was measured (FIG. 12, Circuit A).

Following that, a conductive glass serving as a charge amplifier sensor was connected between the equivalent circuit and the negative input of the amplifier. In order to make this conductive glass act as a capacitor, an aluminum foil was placed below the glass that did not have a conductive coating (FIG. 12, Circuit B).

The effect of inserting the conductive glass-aluminum foil capacitor on the voltage output was evaluated by calculating the difference between the circuits A and B. Similar experiments conducted separately showed an error of 3.3% and 5.7% reduction in the waveform amplitudes between the circuits with and without the conductive glass-aluminum foil capacitor, except for the amplitude, there was not distortion in the waveform itself such as a filter effect.

From this, it was concluded that the conductive glass-aluminum foil capacitor is effective as a sensor for a charge amplifier and can be applied to the measurement of the electrical activity (movement of charged ions inside and outside cells) of cells cultured on the conductive glass.

The circuit C in FIG. 12 shows a layout circuit when an actual cell was used. As a sample, the spontaneous action potential of the cells was measured from the same cells (Nav1.5/Kir2.1 HEK cells) used in the above Reference Example 2 using a charge amplifier. Based on the principle of the charge amplifier, it was confirmed that the intracellular membrane potential change can be measured by amplifying it with an extracellular recording device (FIG. 12, Circuit C).

(1-2) Recording of Cardiomyocyte action potentials using the charge amplifier

In this example, changes in the intracellular membrane potential caused by intracellular action potentials and the like are regarded as changes in charge through the conductive nanoparticles, and this change in charge signal (movement of charged ions ($Na^+$, $K^+$, $Ca^{2+}$, $Cl^-$) in and out of cells due to action potential generation) is applied to the principle of the charge amplifier in this example. And it is measured as a voltage signal (FIG. 13).

More specifically, cardiomyocyte (iCell Cardiomyocyte: CDI) was seeded on a conductive glass (thickness: 2 mm) and cultured using "iCell Cardiomyocytes Maintenance Medium" as a culture solution. Gold-coated magnetic nanoparticles were introduced into myocardial cells using Streptolysin O (SLO, Wako Pure Chemical Industries) by the following method.

That is, cells were washed once with PBS8-(−), replaced with nanoparticle-SLO mix (20 ul PEG-Gold coated magnetic nanoparticle, 5 μl 5×HBPS, 1 μl (1U) activated SLO) solution and incubated (held at 37° C. for 15 minutes). After that, the solution was replaced with iCell Cardiomyocytes Maintenance Medium (inactivation of SLO by serum), and the experiment was conducted on the following day and thereafter.

Similar to the circuit C in (1-1) above, the upper surface of the conductive glass covered with the myocardial-like cells, in which the gold-coated magnetic nanoparticles are incorporated, is connected to the positive input terminal of the amplifier, and the aluminum foil arranged on the lower surface of the glass is connected to the ground input terminal (earth). A capacitor was formed from the upper surface of conductive glass and the aluminum foil on the lower surface, and the electrical activity (movement of charged ions inside and outside the cell) of cells cultured on the upper surface was measured. (FIG. 14).

As described above, in the present invention, it was demonstrated for the first time that the spontaneous action potential of cells can be measured by the conductive nanoparticles using the principle of the charge amplifier.

(Example 2) Recording from Cells with Weak Adhesion Using the Charge Amplifier Mode (CHargeAmpLifier (CHAMPL) Mode)

In this example, typical myocardial cells (iCell Cardiomyocyte2) were used as cells having low adhesion efficiency to the conductive glass surface, and after culturing on the conductive glass surface prepared by the method of Reference Example 6, gold-coated magnetic nanoparticles were introduced into the cells, and the cell membrane was penetrated by a magnetic field. The action potential was evoked and recorded by applying a sodium channel opener such as Veratridine. This experiment was conducted at room temperature.

More specifically, first, a gel-like collagen (Atelocollagen, Koken Co., Ltd.) was applied in a circle of about 5 mm in diameter at the center of the surface of the conductive glass. this collagen was then stretched to form a lattice-like collagen coating film with a spacing of about 0.5 μm using a microelectrode with the tip melted.

Next, cardiomyocyte-like cells (iCell Cardiomyocyte2) were seeded on the surface of the conductive glass and cultured in a cardiomyocyte-specific medium (iCell Cardiomyocytes Maintenance Medium) for about 6 days to form a cardiomyocyte sheet.

Next, gold-coated magnetic nanoparticles were introduced into cells using SLO, and the nanoparticles were attracted to penetrate the cell membrane by a magnetic field generated by a magnet below the conductive glass and brought into contact with the conductive glass electrode. Two days later, the culture medium was replaced with physiological saline, and the action potential of the cells was recorded at room temperature using the charge amplifier mode (CHargeAmpLifier (CHAMPL) mode) (FIG. 14).

However, since no spontaneous action potential was observed in this preparation (data not shown), to induce the action potentials Veratridine (Sigma-Aldrich), which acts as a sodium channel opener, was administered in saline to a final concentration of 100 μM. And the effects of veratridine was recorded. Slow depolarization was observed in the first 40 seconds of veratridine administration, then it was followed by spontaneous action potentials (FIG. 15).

(Example 3) Measurement of Intracellular Potential in Cultured Nerve Cells

The purpose of this example is to confirm that the intracellular potentials from cultured nerve cells in which gold-coated magnetic nanoparticles are penetrated into the cell membrane according to the method of Reference Example 2, can be measured by using a magnet electrode having a capacitive potential measurement function.

(3-1) Preparation of Cultured Nerve Cells

NG108-15 cells were used for the purpose of showing that recording is possible from cultured nerve cells. NG108-15 cells (neuroblastoma-glioma hybrid cells) were cultured in a culture medium containing DMEM (Sigma-Aldrich), HAT supplement (Thermofisher) and 10% FBS (Biowest). NG108-15 was seeded on a cover glass that was coated with 0.1% Polyethyleneimine (pH8.4, 150 mM Sodium Tetra-Borate (Wako)), and cultured in the culture medium, in which FBS concentration was reduced to 5% from the above culture medium, and the nerve differentiation was induced by adding 500 μM Ibuprofen (Wako). The following experiment was conducted 5 days after nerve induction.

(3-2) Penetration of Gold-Coated Magnetic Nanoparticles into the Cell Membrane by the Magnet Electrode Method PEI and PEG-gold coated magnetic nanoparticles were mixed and left at room temperature for 3 hours. This mixed solution is moved to the cell-adhesive surface of the neodymium magnet and left for additional 15 minutes to magnetically bond the gold nanoparticles to the neodymium magnet electrode.

The above nanoparticle-bonding magnet electrode was placed on the cultured cells placed on an iron plate. The magnet electrode is self-sustained and fixed on the cell by the magnetic force generated between the iron plate under the cell and the magnet electrode. The gold nanoparticles on the surface of the magnet electrode penetrated by the action of PEI so that one end was exposed inside the cell.

As a magnet electrode, a neodymium magnet with a magnetic force of 220 millitesla and a diameter of 6 mm was used. A magnet electrode-type capacitance type potential measurement device is formed in which a magnet electrode (MagEle) whose surface other than the cell contact surface is covered with parafilm is connected to a positive input, and a ferromagnetic material placed on the parafilm is connected to a negative pole. At this time, it was confirmed that the parafilm between the ferromagnetic material and the magnet electrode was made thick to ensure complete insulation (FIG. 16A).

Here, recording was performed using the above nanoparticle-bonding magnet electrode (C-M electrode) with added function as capacitance type potential measurement device.

(3-3) Preparation of Cells Using Polycarbonate Cell Culture Insert

Here, except that the neural hybridoma cells (NG108-15 cells) were seeded and cultured in a Polycarbonate cell culture insert (pore size 0.4 μm, Thermo Scientific) instead of the cover glass used in (3-1), conductive nanoparticles (gold nanoparticles) were prepared by the same method as in the above (3-1) and (3-2), and then the cell membrane were penetrated by the conductive nanoparticles (FIG. 16B).

The advantage of using cell culture insert is that the cells are cultured on a polycarbonate permeable membrane with a pore size of 0.4 μm (Thermo Scientific). Even if the upper surface of the cell is covered with the magnet, the solution can be replaced through the gap below the insert. It is also applicable to observe the action of a drug and to measure the activity of ligand gated channel by administering Agonist.

(3-4) Recording of Intracellular Potential of Cultured Nerve Cells

Figure 17A:
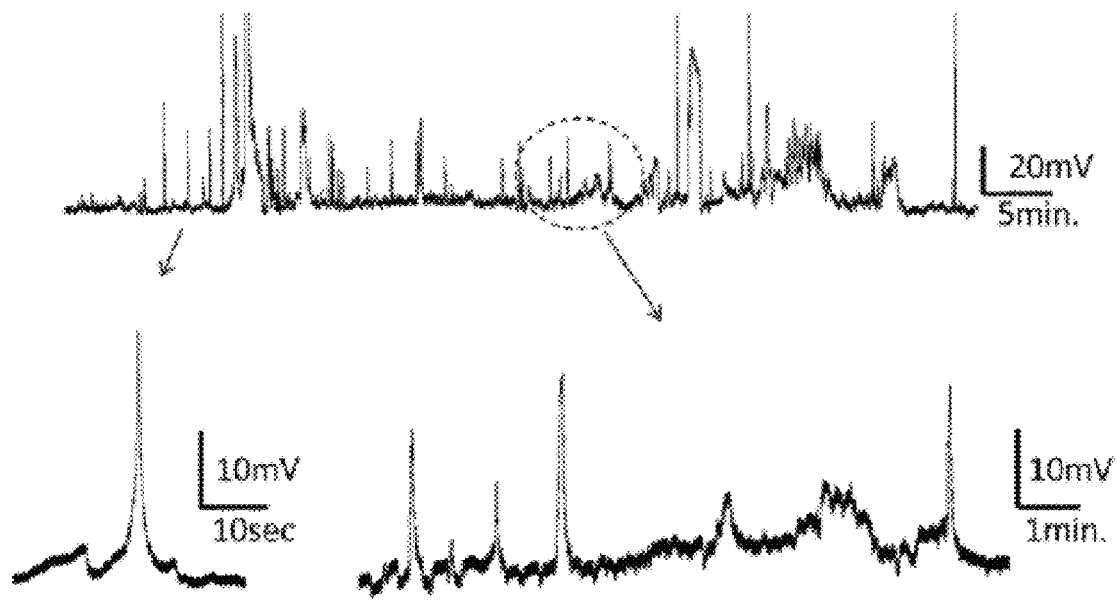

After inducing neural differentiation of NG108-15 cells for 5 days, the culture medium was replaced with extracellular fluid (physiological saline), and an action potential recording experiment was performed. Spontaneous action potentials were recorded by placing C-M electrode on cells seeded on coverslips. Since this method strongly depends on the spontaneous activity of cells, the degree of neural differentiation greatly affects the success of the experiment (FIG. 17A).

Figure 17B:
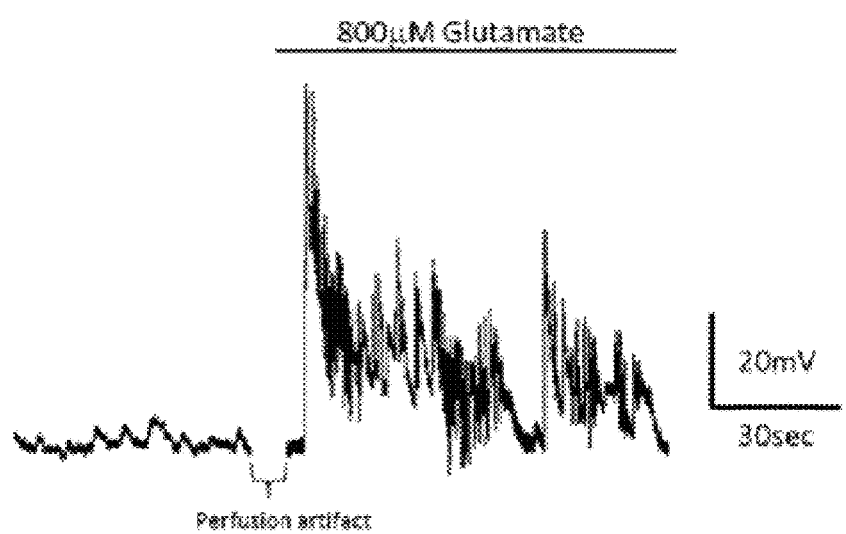

In addition to the spontaneous action potential, the following experiment was conducted to confirm whether the neuronal activity by the neurotransmitter glutamate can be recorded. Experiments were carried out using NG108-15 cells that had been subjected to neural differentiation induction for 2 days. Similar to the above experiment, C-M electrode was placed on the cells and the experiment was performed. Glutamic acid was administered to the extracellular fluid (final external fluid concentration 800 μM), and the response mediated by glutamate receptors was recorded. Glutamate activated the endogenous glutamate receptor, which was recorded as a depolarization (upward change) response of the membrane potential. The membrane potential change induced by glutamate decayed slowly due to desensitization and returned to baseline after about 90 seconds. The baseline and glutamate response artifacts on the figure were removed (FIG. 17B).

Since slow changes in membrane potential that last for several seconds can be recorded, this method can also be used to record changes in membrane potential due to ion channels activated by neurotransmitters and G channel-mediated ion channel activity.

(Example 4) Measurement of Intracellular Potential in Cells Transiently Expressing Ion Channels A myocardial action potential model cell was prepared by transiently expressing a myocardial ion channel genes (SCN5A (Nav1.5), CACNα1C (Cav1.2), and KCNH2) together with a photoreceptor channel (ChRWR) gene (provided by Professor Yao) in cultured CHO cells.

Next, as in Example 2, gold-coated magnetic nanoparticles were introduced using SLO, the nanoparticles were penetrated into the cell membrane by a magnetic field. Then a photoreceptor channel (ChRWR) was stimulated by blue LED light irradiation (Manual irradiation for about 0.5 seconds). Action potential was triggered by membrane depolarization by photoreceptor channel activation. The action potential was recorded using the charge amplifier mode (CHarge AMPLifier (CHAMPL) mode) (FIG. 13) used in Example 2.

In the charge amplifier mode at that time, the (+) electrode is connected to the conductive glass on the cell seeding surface, and the (−) electrode is connected to the strip-shaped aluminum foil placed below the conductive glass. In addition, it is essential that the aluminum foil is installed directly under the cell to be recorded, and if it is installed in a portion apart from the recording cell, an electric signal cannot be detected.

As a result, administration of 500 nM Nifedipine suppressed the calcium channel and decreased the amplitude of action potential.

Furthermore, when the sodium channel was suppressed by administration of 10 mM Lidocaine, all action potentials disappeared, and only the response by the photoreceptor channel was observed. (FIG. 18; Timing of LED irradiation is indicated as the mark "0".)

(Example 5) Measurement of Changes in the Intracellular Potential in Differentiated Cultured Nerve Cells In this experiment, the cultured nerve cells (NG108-15 cells) used in Example 3 were induced and differentiated into nerves under the same differentiation conditions as in the experiment example 3. In the same manner as in Example 3, the MagEle (magnet electrode) is moved from above the target cell toward the cell, and the conductive gold-coated magnetic nanoparticles adsorbed on the MagEle are adhered to the cell membrane to penetrate it. Then, the intracellular potential was measured by connecting the MagEle to the (+) pole and a conductor provided on an insulator (parafilm film) that completely covers the upper surface of the MagEle to the ground. At that time, although the insulator completely covered the top and sides of the (+) pole MagEle, the surface facing the cover glass, to which the cells adhere was not covered, and the cells were not isolated from the external fluid (FIG. 19).

The NG108-15 cells were differentiated by culturing for 3 weeks in DMEM/HAT medium containing 2% FBS supplemented with Forskolin (10 μM).

As a result, a spontaneous action potential was induced by 20 μM Veratridine and suppressed by administration of sodium channel blocker, 3 mM Lidocaine (FIG. 20).

This indicates that the reagent administered extracellularly acted on the activity of NG108-15 cells during recording by MagEle.

In this experimental example, the magnitude of action potential was observed to be smaller than that of the other experimental examples. Such a phenomenon occurs when the electrode resistance is very high. This is considered to be a phenomenon that occurs when the efficiency of the conductive nanoparticles to be transmembrane is low in the cell to be recorded, and this point also acts as an advantage of the capacitive membrane potential measurement. That is, since the charge is expressed by the product of the voltage and the membrane capacitance, Q=VC (Q: Electric Charge, V: Voltage, and C: Membrane Capacitance), even if the voltage change is small due to the influence of the high electrode resistance, if the cells (membrane capacitance) are large enough, it can be detected as a change in charge (Q).

Further, in the result shown in FIG. 20, the fluctuation-like movement of the baseline is extremely small. This suggests that MagEle has a slight AC filtering effect. It is considered that such a phenomenon occurs because the condenser capacitance value was low because the distance between the MagEle and the ground on which the clip was made was too short. In order to prevent the AC filter action, it is desirable to ensure a sufficient capacitor capacity value by combining not only parafilm but also (conductive) glass (infinite resistance) used in (FIG. 12) and other materials with a high resistance value of about 1 mm.

INDUSTRIAL AVAILABILITY

The present invention is particularly useful for drug discovery screening because it can measure intracellular potential easily and accurately. Not only in cultured cardiomyocytes but also in cultured nerve cells, it is expected to make a dramatic contribution to electrophysiological research in vitro.

Further, since the present invention has a simple basic principle, it can be supplied at a relatively low cost, and can be expected to be applied to electrophysiology student training, basic research, and the like.

The invention claimed is:

1. A capacitance-type potential measurement device capable of recording intracellular potential or potential change of target cells, comprising a first conductor, a second conductor, a magnet, and a charge amplifier,
   wherein the first conductor and the second conductor form a capacitor,
   wherein the device forms a potential recording circuit by connecting the first conductor to a positive input of the charge amplifier and by connecting the second conductor to a negative input of the charge amplifier,
   wherein the first conductor comprises a conductive plate and conductive magnetic nanoparticles,
   wherein the conductive plate is disposable below the target cells,
   wherein an upper surface of the conductive plate is in contact with an end of the conductive magnetic nanoparticles penetrating a lower surface of the cell membrane in the target cells;
   wherein the magnet is placed below the conductive plate, and
   wherein the second conductor is a conductive sheet placed between the conductive plate and the magnet.

2. A capacitance-type potential measurement device capable of recording intracellular potential or potential change of target cells comprising: a first conductor and a second conductor, one of the first and second conductors contactable with an end of conductive magnetic nanoparticles penetrating cell membranes of the target cells;
   wherein the first conductor is a magnet electrode disposable above the target cells, wherein a lower surface of the magnet electrode is contactable with the end of the conductive magnetic nanoparticles penetrating the target cells and an upper surface and side surfaces of the magnet electrode are covered with an insulator; and
   wherein the second conductor is a magnetic body or a magnet-attracting metal plate on the upper surface of the magnet electrode.

3. The capacitance-type potential measurement device according to claim 2, in combination with a culture dish to retain the target cells and extracellular fluid therein, wherein the insulator covering the side surfaces of the magnet electrode is not completely fixed to a bottom of the culture dish, and the target cells in contact with the lower surface of the magnet electrode are not fully separated from extracellular fluid.

4. The capacitance-type potential measurement device according to claim 3, in combination with a porous membrane, wherein target cells, in contact with the lower surface of the magnet electrode, are adhered to the porous membrane disposable above the culture dish, thereby allowing extracellular fluid to diffuse and flow between the culture dish and the porous membrane.

5. The capacitance-type potential measurement device according to claim 4, wherein the porous membrane is disposed at a bottom surface of a cell culture insert, and extracellular fluid is perfused between the porous membrane at the bottom surface of the cell insert and the culture dish.

* * * * *

UNITED STATES PATENT AND TRADEMARK OFFICE
CERTIFICATE OF CORRECTION

| | | |
|---|---|---|
| PATENT NO. | : 12,247,972 B2 | |
| APPLICATION NO. | : 17/050759 | |
| DATED | : March 11, 2025 | |
| INVENTOR(S) | : Mitsuyoshi Saito | |

It is certified that error appears in the above-identified patent and that said Letters Patent is hereby corrected as shown below:

On the Title Page

Item (71) Applicant:
Include the following as a co-Applicant:
-- Mitsuyoshi SAITO, Tokyo (JP) --

Signed and Sealed this
Twenty-fourth Day of June, 2025

Coke Morgan Stewart
*Acting Director of the United States Patent and Trademark Office*